(12) United States Patent
Lee et al.

(10) Patent No.: US 10,279,352 B2
(45) Date of Patent: May 7, 2019

(54) PCR MODULE, PCR SYSTEM HAVING THE SAME, AND METHOD OF INSPECTING USING THE SAME

(71) Applicant: OPTOLANE Technologies Inc., Seongnam-shi, Gyonggi-do (KR)

(72) Inventors: DoYoung Lee, Seoul (KR); In Gyun Jeon, Seongnam-shi (KR); An Shik Choi, Seoul (KR); Kyung Hak Choi, Yongin-shi (KR)

(73) Assignee: OPTOLANE TECHNOLOGIES INC., Seongnam-shi, Gyonggi-Do (KR)

( * ) Notice: Subject to any disclaimer, the term of this patent is extended or adjusted under 35 U.S.C. 154(b) by 371 days.

(21) Appl. No.: 15/064,816

(22) Filed: Mar. 9, 2016

(65) Prior Publication Data
US 2016/0271611 A1    Sep. 22, 2016

(30) Foreign Application Priority Data

Mar. 18, 2015  (KR) .......................... 10-2015-0037725
Feb. 19, 2016  (KR) .......................... 10-2016-0020053

(51) Int. Cl.
| C12P 19/34 | (2006.01) |
| B01L 7/00 | (2006.01) |
| C12Q 1/686 | (2018.01) |
| B01L 3/00 | (2006.01) |
| G01N 21/64 | (2006.01) |

(52) U.S. Cl.
CPC ............. B01L 7/52 (2013.01); B01L 3/50851 (2013.01); C12Q 1/686 (2013.01); G01N 21/64 (2013.01); B01L 2200/028 (2013.01); B01L 2200/147 (2013.01); B01L 2300/0663 (2013.01); B01L 2300/0681 (2013.01); B01L 2300/0819 (2013.01); B01L 2300/18 (2013.01); B01L 2300/1805 (2013.01); B01L 2300/185 (2013.01); B01L 2300/1822 (2013.01); B01L 2300/1844 (2013.01)

(58) Field of Classification Search
CPC ......... B01L 2200/028; B01L 2200/147; B01L 2300/0663; B01L 2300/0681; B01L 2300/0819; B01L 2300/18; B01L 2300/1805; B01L 2300/1844; B01L 3/50851; B01L 7/52; C12Q 1/686; G01N 21/64
USPC ....................................................... 435/91.2
See application file for complete search history.

(56) References Cited

U.S. PATENT DOCUMENTS

| 7,338,637 B2 | 3/2008 | Pease et al. |
| 7,799,557 B2 | 9/2010 | Oh et al. |
| 8,697,433 B2 | 4/2014 | Oh et al. |
| 2006/0246580 A1 | 11/2006 | Kim et al. |
| 2010/0297640 A1 | 11/2010 | Kumar et al. |
| 2011/0308313 A1 | 12/2011 | Azimi et al. |
| 2012/0309636 A1* | 12/2012 | Gibbons ............... B01L 3/0275 506/9 |
| 2014/0001041 A1 | 1/2014 | Rahman et al. |
| 2014/0287414 A1 | 9/2014 | Chung et al. |
| 2014/0329224 A1 | 11/2014 | Arnold et al. |
| 2014/0329244 A1* | 11/2014 | Ding .................... C12Q 1/6806 435/6.12 |

FOREIGN PATENT DOCUMENTS

| EP | 1 541 237 | 6/2005 |
| KR | 10-2005-0106408 | 11/2005 |
| KR | 10-0668320 | 1/2007 |

OTHER PUBLICATIONS

Dmitry A. Khodakov et al., "An oligonucleotide microarray for multiplex real-time PCR identification of HIV-1 HBV, and HCV"; BioTechniques, vol. 44, No. 2, 2008, pp. 241-248.
Huan Huang et al., "A gel-based solid-phase amplification and its application for SNP typing and sequencing on-chip"; The Royal Society of Chemistry, Analyst, 2009, 134, pp. 2434-2440.
European Search Report for European Application No. 16 16 0789, dated Dec. 9, 2016.
Haig Norian et al., "An integrated CMOS quantitative-polymerase-chain-reaction lab-on-chip for point-of-care diagnostics"; The Royal Society of Chemistry, Lab on a Chip, Aug. 15, 2014, vol. 14, pp. 4076-4084.
Brian J. Taylor et al., "A lab-on-chip for malaria diagnosis and surveillance"; Malaria Journal, 2014, 13:179, pp. 1-10.
Nan Guo et al., "CMOS Time-Resolved, Contact, and Multispectral Fluorescence Imaging for DNA Molecular Diagnostics"; Sensors 2014, Oct. 31, 2014, pp. 20602-20619.

* cited by examiner

*Primary Examiner* — Cynthia B Wilder
(74) *Attorney, Agent, or Firm* — Kile Park Reed & Houtteman PLLC

(57) ABSTRACT

A polymerase chain reaction (PCR) module is detachably combined with a reader system. The reader system includes a central processing unit (CPU) receiving a photo sensing signal to calculate gene amplification amount in real time and generating a temperature control signal based on a temperature signal and a temperature control information. The PCR module includes a photo sensor assembly, a partition wall, and an interface module. The photo sensor assembly includes a plurality of photo sensors and a temperature sensor. The photo sensors are arranged in an array shape to sense emission light generated from a specimen to generate the photo sensing signal. The partition wall is protruded from the photo sensor assembly to define a reaction space in which the specimen is received. The interface module is electrically connected to the photo sensor assembly to transmit the photo sensing signal and the temperature signal to the reader system.

16 Claims, 32 Drawing Sheets

PCR MODULE, PCR SYSTEM HAVING THE SAME, AND METHOD OF INSPECTING USING THE SAME

CROSS-REFERENCE TO RELATED APPLICATION(S)

This application claims priority under 35 USC § 119 to Korean Patent Applications No. 10-2015-0037725, filed on Mar. 18, 2015 and No. 10-2016-0020053, filed on Feb. 19, 2016 in the Korean Intellectual Property Office (KIPO), the contents of which are incorporated herein in its entirety by reference.

BACKGROUND

1. Technical Field

Example embodiments relate generally to a PCR module, a PCR system including the same, and a method of inspecting using the same. More particularly, embodiments of the inventive concept relate to a PCR module capable of detachably combined with a reader system which is capable of inspecting in real time, a PCR system including the same, and a method of inspecting using the same in real time.

2. Description of the Related Art

Gene amplification technology is an essential process in molecular diagnosis, and is a technology of repetitively copying and amplifying a specified nucleotide sequence of minute deoxyribonucleic acid (DNA) or ribonucleic acid (RND) in a specimen. Among the above, polymerase chain reaction (PCR) is a representative gene amplification technology. The PCR includes three stages of denaturation of DNA, annealing of primer, and extension of DNA, and each of the stages depends on temperature of the specimen. Thus, the temperature of the specimen is repetitively changed to amplify DNA.

Real-time PCR is a method capable of monitoring an amplification state of a specimen in an amplification process in real time. The real-time PCR senses intensity of fluorescence which is changed by amplified amount of DNA to quantitatively analyze the DNA. A conventional real-time PCR device, generally, includes a heat transfer element, a heat transfer block, a light source part, and a light receiving part. The heat transfer block transmits heat to a tube in which the specimen is disposed. The light source part irradiates an excitation light to the specimen in the tube. The light receiving part receives a fluorescence light generated from the specimen.

A currently used real-time PCR device of a table top shape includes an optical part of about 80% of a total volume. The optical part senses the fluorescence light of the specimen. Thus, mobility is nearly zero, so that point-of-care test is nearly impossible and cost of the device is very high. Also, in case of transportation such as moving, relocation of the device, error is generated so that a light of time is required to rearrange, calibration, etc.

Also, a lot of time is required to set various reagents, and pollution is highly probable. Furthermore, size of the system is very high, and most of the device is configured as an isolated system. Thus, information communication with the outside is hard.

SUMMARY

Some example embodiments provide a PCR module capable of detachably combined with a reader system which is capable of inspecting in real time.

Some example embodiments also provide a PCR system including the PCR module.

Some example embodiments also provide a method of inspecting using the PCR system in real time.

According to some example embodiments, a polymerase chain reaction (PCR) module is detachably combined with a reader system. The reader system includes a central processing unit (CPU), a memory, and an interface. The CPU receives a photo sensing signal to calculate gene amplification amount in real time and generates a temperature control signal based on a temperature signal and a temperature control information. The memory is connected to the CPU to store the gene amplification amount and the temperature control information. The interface is connected to the CPU to transmit the gene amplification amount received from the CPU in real time to an outside or to apply an external input signal to the CPU. The PCR module includes a photo sensor assembly, a partition wall, and an interface module. The photo sensor assembly includes a plurality of photo sensors and a temperature sensor. The photo sensors are arranged in an array shape to sense emission light generated from a specimen to generate the photo sensing signal. The temperature sensor senses temperature to output the temperature signal. The partition wall is protruded from the photo sensor assembly to define a reaction space in which the specimen is received. The interface module is electrically connected to the photo sensor assembly to transmit the photo sensing signal and the temperature signal to the reader system.

In example embodiments, the PCR module may further include a light source supplying light to the reaction space, an optical filter disposed on the photo sensor assembly to transmit the emission light, and a cover defining an upper portion of the reaction space and including opaque material.

In example embodiments, the reader system may further include a light source supplying light to the reaction space, and the PCR module may further include a cover defining an upper portion of the reaction space and including transparent material.

In example embodiments, the reader system may further include a temperature control module receiving the temperature control signal to adjust temperature of the reaction space.

In example embodiments, the PCR module may further include a temperature control part receiving the temperature control signal to adjust temperature of the reaction space, and the interface module may receive the temperature control signal to apply the received temperature control signal to the temperature control part.

In example embodiments, the reader system may further include a heat conductor surrounding the PCR module, and a thermostatic member maintaining a constant temperature and exchanging heat with the heat conductor.

In example embodiments, the PCR module may further include a heat conductor receiving the temperature control signal to transmit heat in the reaction space to the outside.

In example embodiments, the PCR module may further include a heating part receiving the temperature control signal to increase temperature of the reaction space.

In example embodiments, one output electrode of the photo sensor may be connected to a plurality of photo sensor units.

In example embodiments, the photo sensor assembly may further include a photo sensor array including a plurality of photo sensors having photo sensor units of different numbers.

In example embodiments, the reader system may be detachably combined with a plurality of PCR modules.

In example embodiments, the PCR module may further include a 3-dimensional (3D) organic pad disposed on the photo sensor assembly. The 3D organic pad may include a hydrophilic material being not melted or dissolved but being cross-linked by high polymer chains or polymer chains to form a 3D structure when mixed with water, and a primer being a small DNA attached to an area adjacent to gene nucleotide sequence to be amplified, and being a starting DNA when polymerase amplifies DNA.

In example embodiments, the 3D organic pad may include a hydrogel pad or a spin on glass (SOG) pad.

In example embodiments, the photo sensor assembly may be electrically connected to the interface module through wire bonding.

In example embodiments, the photo sensor assembly may be electrically connected to the interface module through a through silicon via (TSV).

According to some example embodiments, a PCR system includes a reader system and a PCR module. The reader system includes a central processing unit (CPU), a memory, and an interface. The CPU receives a photo sensing signal to calculate gene amplification amount in real time and generating a temperature control signal based on a temperature signal and a temperature control information. The memory is connected to the CPU to store the gene amplification amount and the temperature control information. The interface is connected to the CPU to transmit the gene amplification amount received from the CPU in real time to an outside or to apply an external input signal to the CPU. The PCR module is detachably combined with the reader system. The PCR module includes a photo sensor assembly, a partition wall, and an interface module. The photo sensor assembly includes a plurality of photo sensors and a temperature sensor. The photo sensors are arranged in an array shape to sense emission light generated from a specimen to generate the photo sensing signal. The temperature sensor senses temperature to output the temperature signal. The partition wall is protruded from the photo sensor assembly to define a reaction space in which the specimen is received. The interface module is electrically connected to the photo sensor assembly to transmit the photo sensing signal and the temperature signal to the reader system.

In example embodiments, the reader system may further include a second temperature control module decreasing temperature of the PCR module using the temperature control signal, and the PCR module may further include a first temperature control part increasing temperature of the PCR module using the temperature control signal.

According to some example embodiments, a method of inspecting using a PCR system is provided. The PCR system includes a reader system and a PCR module. The reader system includes a central processing unit (CPU), a memory, and an interface. The CPU receives a photo sensing signal to calculate gene amplification amount in real time and generates a temperature control signal based on a temperature signal and a temperature control information. The memory is connected to the CPU to store the gene amplification amount and the temperature control information. The interface is connected to the CPU to transmit the gene amplification amount received from the CPU in real time to an outside or to apply an external input signal to the CPU. The PCR module is detachably combined with the reader system. The PCR module includes a photo sensor assembly, a partition wall, and an interface module. The photo sensor assembly includes a plurality of photo sensors and a temperature sensor. The photo sensors are arranged in an array shape to sense emission light generated from a specimen to generate the photo sensing signal. The temperature sensor senses temperature to output the temperature signal. The partition wall is protruded from the photo sensor assembly to define a reaction space in which the specimen is received. The interface module is electrically connected to the photo sensor assembly to transmit the photo sensing signal and the temperature signal to the reader system. In the method of inspecting using the PCR system, specimen information is input. The specimen information is matched with reagent information. A PCR module including a reagent matched with the reagent information is manufactured. The specimen is injected into the PCR module to mount the PCR module into the reader system to inspect the specimen.

In example embodiments, the matching the specimen information and the reagent information may include searching previously stored reagent information to determine existence of the reagent matched with the specimen information.

In example embodiments, the method may further include when reagent matched with the specimen information does not exist among previously stored reagent information, the reagent information may be transmitted to terminals of a plurality of reagent developers, and a developer of the reagent may be selected through information responded from the terminal of the reagent developer to develop the reagent.

According to some example embodiments, the PCR system includes a PCR module and a reader system. The PCR module includes a photo sensor assembly, a 3D organic pad, and a reaction container. The photo sensor assembly includes a plurality of photo sensors arranged in an array shape. The 3D organic pad is disposed on the photo sensor assembly, and includes hydrophilic material and a primer. When the hydrophilic material is mixed with water, the hydrophilic material is not dissolved or melted but high polymer chains or polymer chains are cross-linked to maintain a 3D structure. The primer is a small DNA attached to an area adjacent to gene nucleotide sequence to be amplified, and is a starting DNA when polymerase amplifies DNA. The reaction container is disposed on the photo sensor assembly and receives the 3D organic pad. The reader system includes a CPU, a memory, and an interface. The CPU receives a photo sensing signal from the PCR module to calculate gene amplification amount in real time, and receives a temperature signal corresponding to temperature of the reaction container to compare the received temperature signal with a temperature control information, thereby generating a temperature control signal. The memory is connected to the CPU to store the gene amplification amount and the temperature control information. The interface is connected to the CPU to transmit the gene amplification amount received from the CPU in real time to an outside or to apply an external input signal to the CPU.

According to some example embodiments, a method of manufacturing a PCR module is provided. The PCR module includes a photo sensor assembly, a 3D organic pad, and a reaction container. The photo sensor assembly includes a plurality of photo sensors arranged in an array shape. The 3D organic pad is disposed on the photo sensor assembly, and includes hydrophilic material and a primer. When the hydrophilic material is mixed with water, the hydrophilic material is not dissolved or melted but high polymer chains or polymer chains are cross-linked to maintain a 3D structure. The primer is a small DNA attached to an area adjacent to gene nucleotide sequence to be amplified, and is a starting DNA when polymerase amplifies DNA. The reaction container is disposed on the photo sensor assembly and receives the 3D organic pad. The PCR module is applied to a PCR system including a reader system. The reader system receives a photo sensing signal to calculate gene amplification amount in real time and to control temperature of the reaction container. In the method of manufacturing the PCR module, firstly the photo sensors are formed on a substrate using a semiconductor process. Then, the 3D organic pad is formed on the substrate on which the photo sensors are formed.

According to some example embodiments, a method of inspecting uses a reader system detachably combined with a PCR module to drive the PCR module. The PCR module includes a reaction container and a photo sensor sensing fluorescent light generated from the reaction container. The reader system includes a CPU, a memory, a temperature control module, and an interface. The CPU receives a photo sensing system from the PCR module to calculate a gene amplification amount in real time, and receives a temperature signal corresponding to a temperature of the reaction container in real time to compare the temperature signal with a temperature control information in real time, thereby generating a temperature signal. The memory is connected to the CPU to store the gene amplification amount and the temperature control information. The temperature control module receives the temperature control signal to adjust temperature of the PCR module. The interface is connected to the CPU to transmit the gene amplification amount received from the CPU in real time or to apply an output input signal to the CPU. In the method of inspecting, firstly specimen information is input. Then, the specimen information is matched with reagent information. Then, a PCR module including a reagent matched with the reagent information. Then, specimen is injected into the PCR module and mounted in the reader system, thereby inspecting the specimen.

According to the present invention, the optical part is embedded into the PCR module, and the PCR module is manufactured in a detachable module shape. Thus, size of the reader system is greatly decreased. Also, size of the PCR module and the reader system is greatly decreased, and manufacturing cost is decreased.

Also, although the reader system is moved, rearrangement, calibration, etc., is not required. Thus, mobility is greatly improved, so that point-of-care inspection is capable. In particular, in an emergency case such as epidemic, identification in disaster, etc., the PCR system may be rapidly introduced, so that damage may be decreased.

Also, the reagent may be embedded into the PCR module, so that additional process for setting the reagent may be omitted. Thus, pollution is greatly decreased, and an additional process for preparing inspection may be omitted.

Also, information communication to the outside may be possible through an internet, etc., so that a system such as an application store or a market may be established by various customers and a plurality of reagent developers. Thus, reagents and information may be exchanged.

Also, the PCR module includes the plurality of hydrogel pads, and different primers are disposed in the hydrogels. Thus, a plurality of gene types may be inspected.

Also, in a conventional multi inspection method, since different wavelengths of fluorescent lights are used, an optical part has complex structure. However, in the embodiment of the present invention, different primers are disposed in the hydrogel pads, so that the multi-inspection may be performed although single fluorescent material is used. Thus, the photo sensor assembly has a simple structure.

Also, the specimens and the buffering agent are alternately disposed in the specimen injection part, so that the specimens may be injected into the plurality of hydrogel pads by the simple operation of pressing the pressure from the one side of the specimen injection part.

Also, in a conventional array method, since genetic material is only disposed on a surface of a pad, the gene amplification speed is very slow. However, the hydrogel pad has the 3D structure of the polymer chains, so that the gene amplification is performed in the hydrogel pad as well as on the surface of the hydrogel pad. Thus, the gene amplification speed is very fast. Thus, the array may be formed by the hydrogel pads, so that the gene amplification may be performed in real time at various positions. Also, the fluorescent light is only generated from the hydrogel pad, so that the amount of light is increased to increase intensity of the signal, thereby realizing more sensitive test.

Also, the PCR module includes the heat conductor and the heating part, so that the temperature of the reaction space may be easily adjusted.

Furthermore, the PCR module may include the plurality of photo sensors having the photo sensor units of different numbers, so that optimized inspection based on the intensity of the light. Thus, accuracy is improved using the signals output from the plurality of photo sensors.

Also, the photo sensor assembly may include the light driving part or the driving circuit part, so that the size of the PCR system may be greatly decreased.

BRIEF DESCRIPTION OF THE DRAWINGS

Illustrative, non-limiting example embodiments will be more clearly understood from the following detailed description taken in conjunction with the accompanying drawings.

DETAILED DESCRIPTION OF THE EMBODIMENTS

Figure 1:
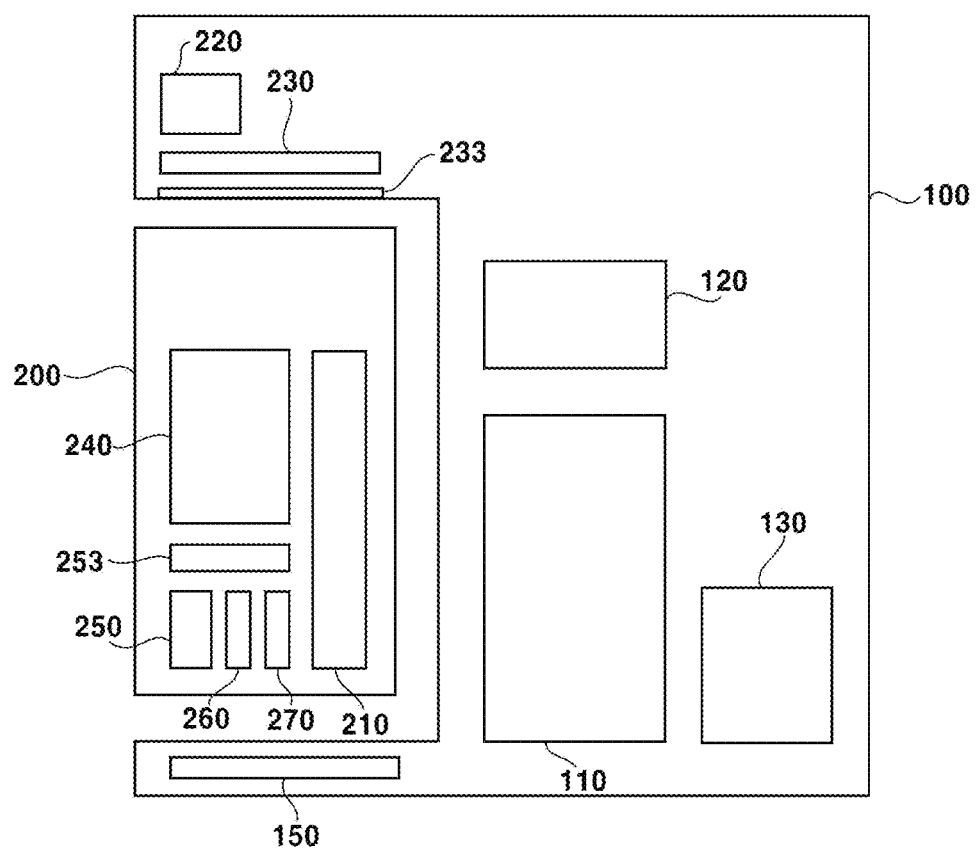
FIG. 1 is a block diagram illustrating a reader system for a PCR module according to one embodiment of the present invention.

Various example embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

It will be understood that, although the terms first, second, third etc. may be used herein to describe various elements, these elements should not be limited by these terms. These terms are used to distinguish one element from another. Thus, a first element discussed below could be termed a second element without departing from the teachings of the present inventive concept. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular example embodiments only and is not intended to be limiting of the present inventive concept. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, a PCR module, a PCR system including the same, and a method of inspecting using the same of the present invention will be explained with reference to the accompanying drawings.

Figure 2:
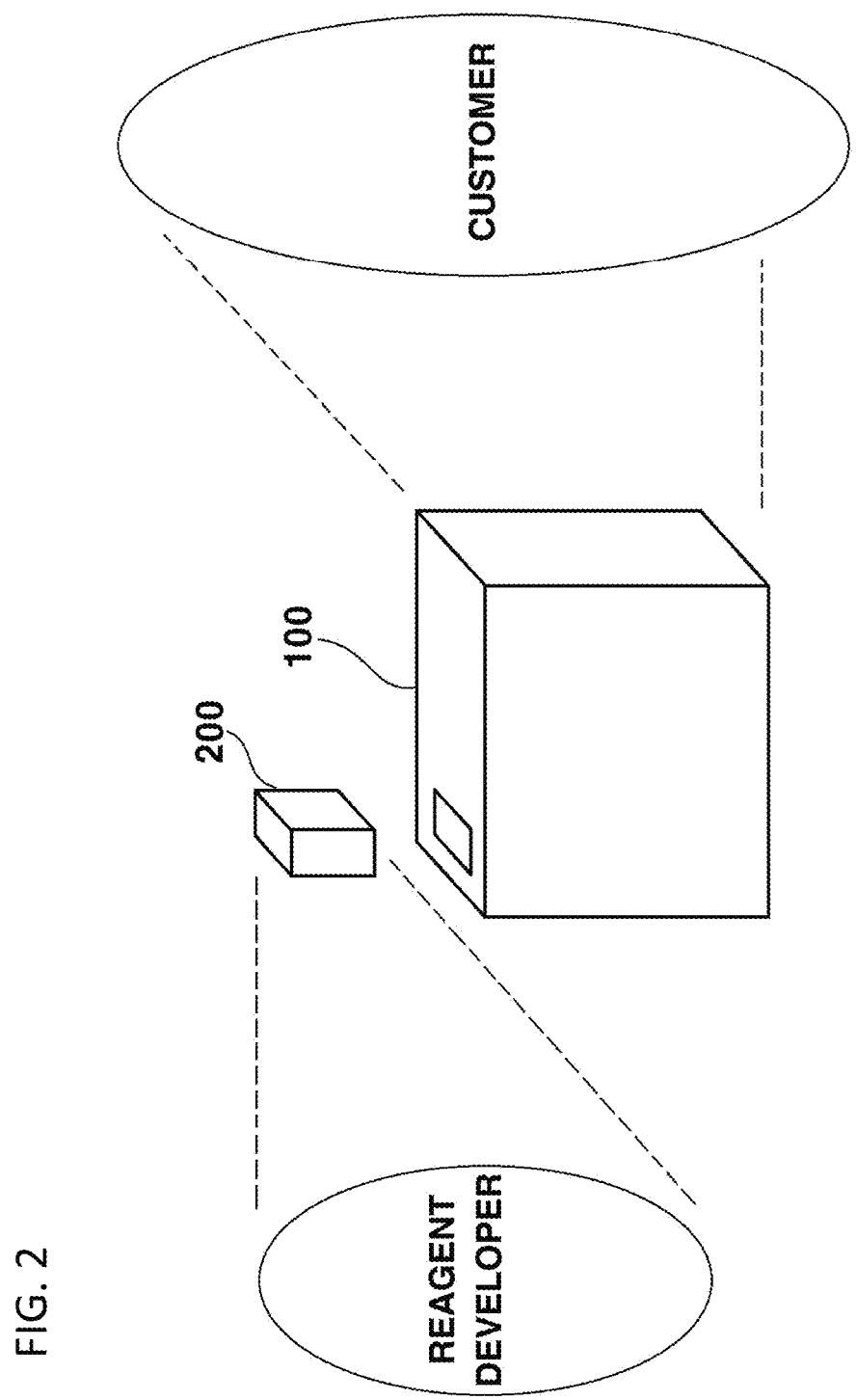
FIG. 2 is a perspective view illustrating the reader system for the PCR module shown in FIG. 1.

FIG. 1 is a block diagram illustrating a reader system for a PCR module according to one embodiment of the present invention. FIG. 2 is a perspective view illustrating the reader system for the PCR module shown in FIG. 1.

Referring to FIGS. 1 and 2, the reader system 100 for the PCR module is detachably combined with the PCR module 200 and operates the PCR module 200. In FIG. 2, one PCR module 200 is combined with the reader system 100. However, the person in the related Art may understood that a plurality of the PCR modules 200 may be simultaneously combined with one reader system 100.

The reader system 100 includes a central processing unit (CPU) 110, a memory 120, an interface 130, a second temperature control part 150, a light source 230, a light source filter 233, and a light source driving part 220.

The CPU 110 reads driving data stored in the memory 120 to drive the second temperature control part 150 and the PCR module 200. Also, the CPU 110 receives photo sensing information, temperature information, etc., from the PCR module 200 and stores the same in real time. The CPU 110 calculates gene amplification amount in real time using the photo sensing information, the temperature information, etc., received from the PCR module 200 to generate information of the gene amplification amount. The CPU 110 stores the information of the gene amplification amount in the memory 120 in real time and transmit the information of the gene amplification amount to the interface 130.

The light source driving part 220 drives the light source 230 using a light source driving signal received from the CPU 110 to drive the light source 230.

The light source 230 generates an excitation light using the light source driving signal.

The light source filter 233 is disposed under the light source 230 to filter the excitation light generated from the light source 230. For example, the light source filter 233 may filter the excitation light to transmit ultraviolet light.

A specimen in the receiving container 240 is inspected using a light having passed through the light source filter 233. In the present embodiment, the light source filter 233 is disposed to minimize noise caused by an external light, thereby decreasing error of the photo sensor 250 by luminance change of the external light.

Figure 3:
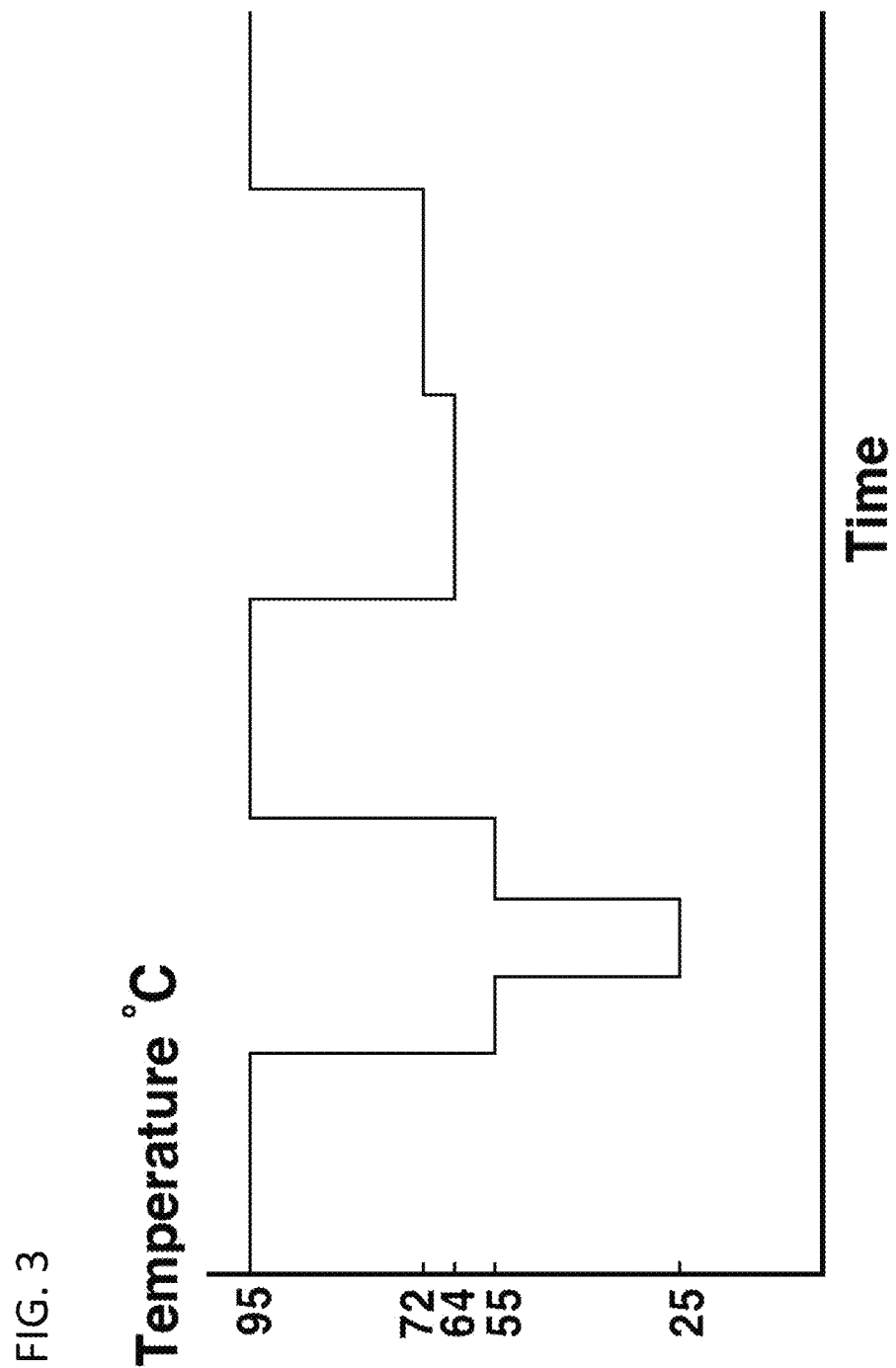
FIG. 3 is a graph illustrating temperature control data of the reader system for the PCR module shown in FIG. 1.

FIG. 3 is a graph illustrating temperature control data of the reader system for the PCR module shown in FIG. 1.

Referring to FIGS. 1 to 3, the temperature control data describes a temperature corresponding to a time corresponding to operation of the PCR module 200. For example, the temperature control data may be 95° C., 55° C., 25° C., 55° C., 95° C., 64° C., or 72° C., and may include data in which the sequentially changing temperatures in time is one cycle.

Figure 4:
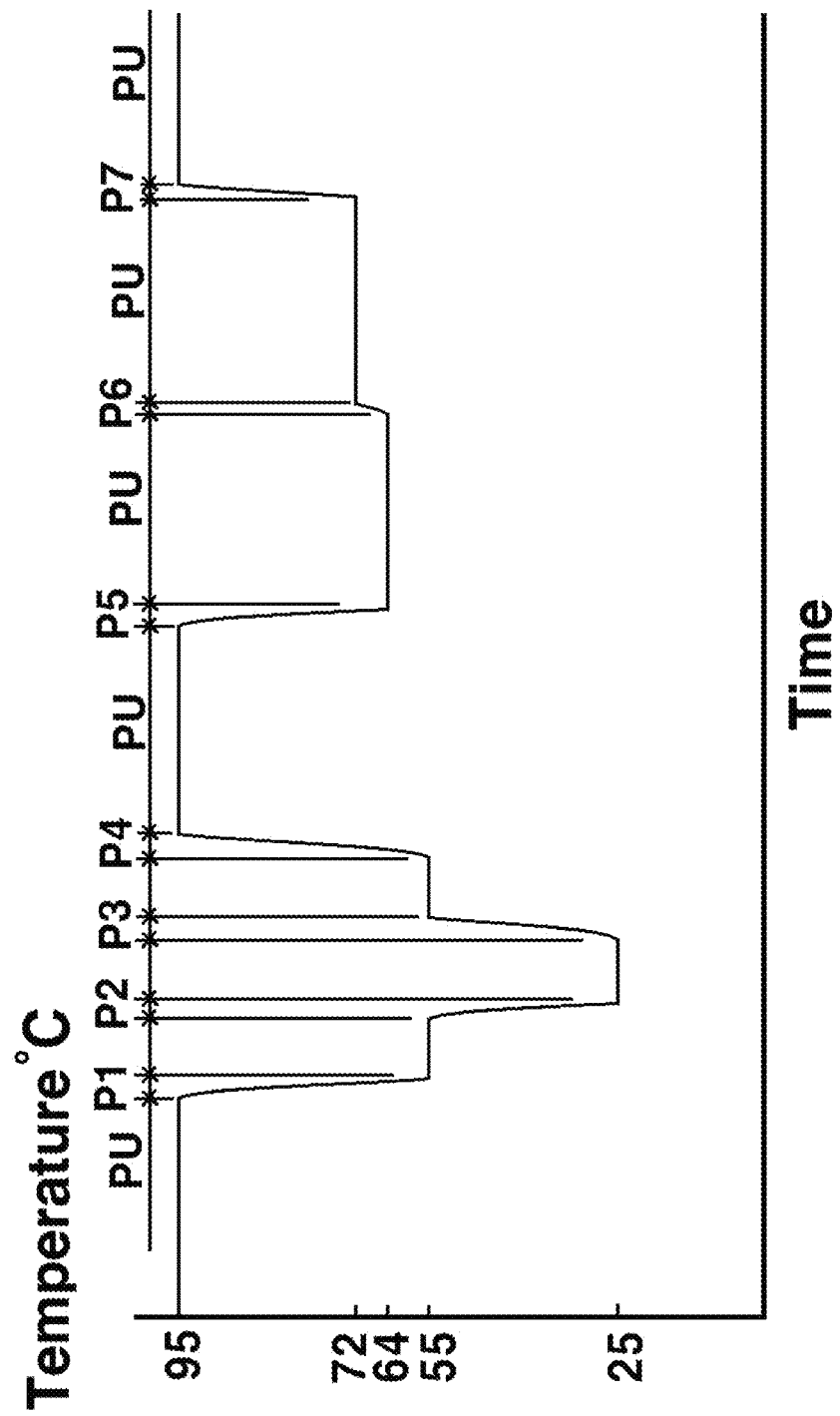
FIG. 4 is a graph illustrating temperature of a reaction container of the PCR module based on control of the reader system for the PCR module shown in FIG. 1.
Figure 5:
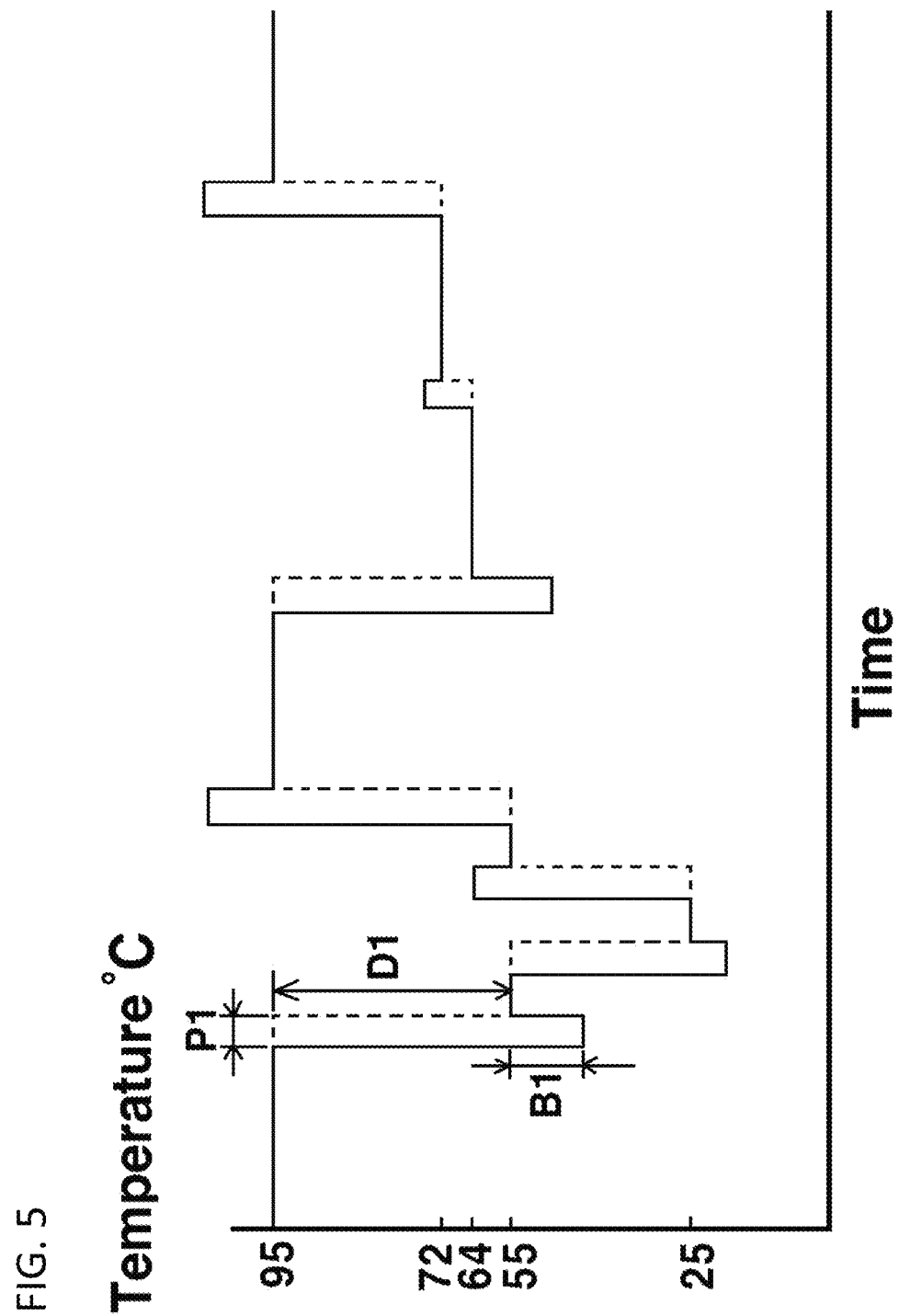
FIG. 5 is a graph illustrating a temperature control signal of the reader system for the PCR module shown in FIG. 1.

FIG. 4 is a graph illustrating temperature of a reaction container of the PCR module based on control of the reader system for the PCR module shown in FIG. 1. FIG. 5 is a graph illustrating a temperature control signal of the reader system for the PCR module shown in FIG. 1.

Referring to FIGS. 1 to 5, the temperature control signal includes a signal for controlling temperature so that the temperature of the receiving container 240 in the PCR module 200 corresponds to the temperature control data. For example, the temperature of the specimen includes a period PU in which the temperature of the specimen maintains a constant temperature, periods P3, P4, P6, and P7 in which the temperature increases, periods P1, P2, and P5 in which the temperature decreases.

The period PU is a period in which the temperature in the reaction container 240 is not changed but maintains the constant temperature. The reaction container 240 has heat insulation characteristics so that the temperature control signal may not be changed. The CPU 110 compares a current temperature of the temperature control data with a current temperature of the reaction container 240. When the temperature of the reaction container 240 is going to be changed, a temperature control signal for heating/cooling is generated, so that the generated temperature control signal is transmitted to the first temperature control part 270 and the second temperature control part 150.

The periods P3, P4, P6, and P7 are periods in which the temperature in the reaction container 240 increases. The PCR module 200 is rapidly heated so that the temperature of the reaction container 240 is increased. In the present invention, in an early period P3 of increasing the temperature, a temperature control signal corresponding to a temperature higher than a target temperature to be increased is generated, so that the reaction container 240 is rapidly heated. In a late period of increasing the temperature, a temperature control signal close to the target temperature is generated. For example, in the beginning of a boosting period P1 corresponding to a temperature change period, the temperature control signal is boosted (B1). The boosted amount B1 may be ⅕ to ½ of a value D1 of temperature change. When the boosted amount B1 is smaller than ⅕ of a temperature change value D1, boosting effect is small so that a time for reaching the target temperature is increased. When the boosted amount B1 is greater than ½ of the temperature change value D1, the boosted temperature is too high so that a portion of the specimen may be deformed.

The periods P1, P2, and P5 are periods in which the temperature in the reaction container 240 rapidly decreases. The PCR module 200 is rapidly cooled so that the temperature of the reaction container 240 is decreased. In the present invention, in an early period of decreasing the temperature, a temperature control signal corresponding to a temperature lower than a target temperature to be decreased is generated, so that the reaction container 240 is rapidly cooled. In a late period of decreasing the temperature, a temperature control signal close to the target temperature is generated.

In the present invention, the early periods of increasing the temperature and the decreasing the temperature, the temperatures of the reaction container 240 are rapidly changed, to prevent deformation of the specimen in the reaction container 240 and to improve credibility of inspection.

The memory 120 is connected to the CPU 110 to drive the second temperature control part 150 and the PCR module 200 using previously stored driving data, and to store the photo sensing information, the temperature information, etc., in real time. The driving data may include temperature control data, photo control data, etc., and may be stored in the memory 120 in a data type, and may be input from the outside through an input device (not shown) and stored. For example, the memory 120 may include various storing devices such as DDR3, SRAM(Frame), SSD(FLASH), etc.

The interface 130 is connected to the CPU 110 to transmit the information of the gene amplification amount received from the CPU 110 in real time or transmit the input signal of the outside to the CPU 110. In the present invention, the interface 130 may include communication systems (not shown) such as wireless LAN (WLAN), WiFi, Bluetooth, etc., data interfaces (not shown) such as universal serial bus (USB), inter-integrated circuit (I$^2$C), universal asynchronous receiver/transmitter (UART), pulse width modulation (PWM), low voltage differential signaling (LVDS), mobile industry processor interface (MIPI), etc., display devices (not shown) such as a liquid crystal display (LCD), an organic light emitting display (OLED), a cathode ray tube (CRT), etc., input devices (not shown) such as a mouse, a keyboard, etc., output devices (not shown) such as a printer, a fax, etc.

The second temperature control part 150 is connected to the CPU 110 to control the temperature of the PCR module 200 using the temperature control data received from the CPU 110.

Figure 6:
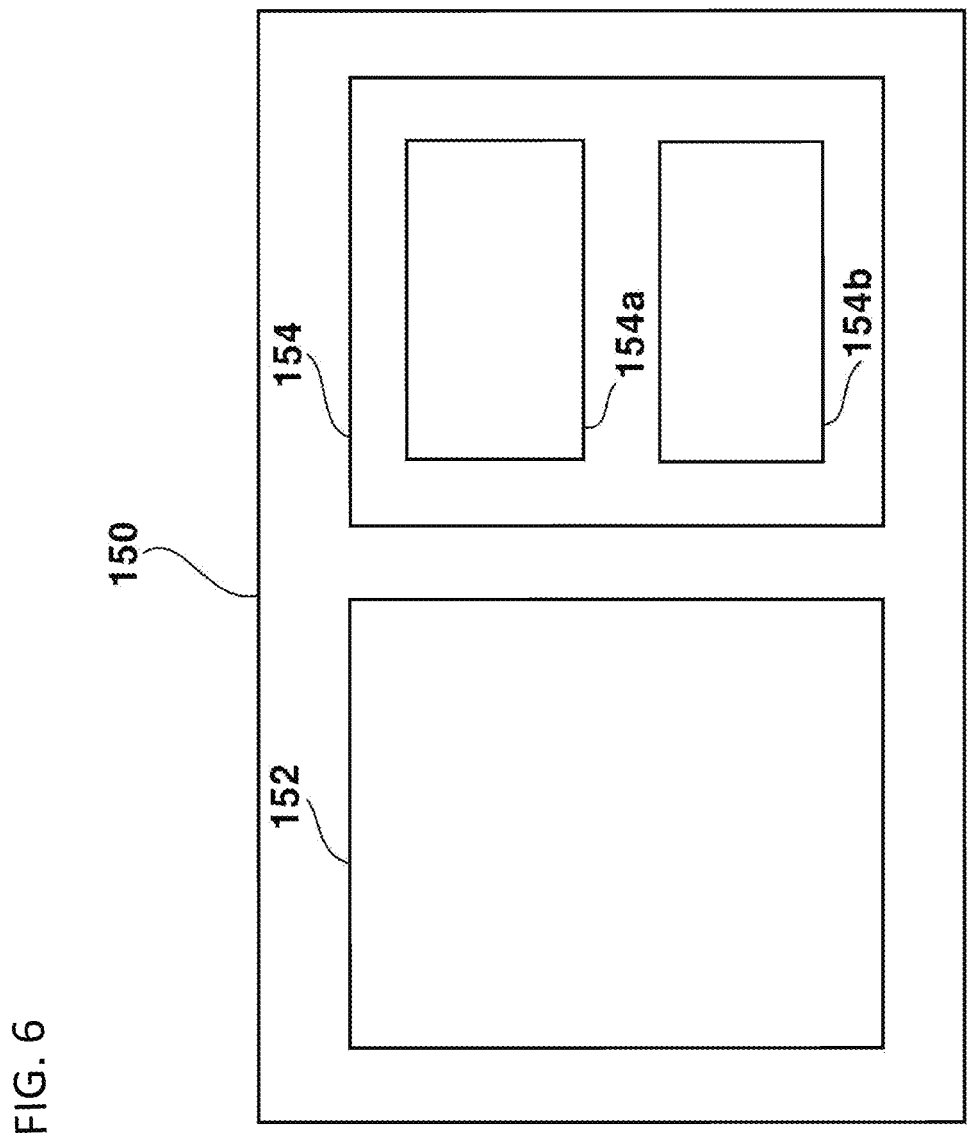
FIG. 6 is a block diagram illustrating a second temperature control part shown in FIG. 1.

FIG. 6 is a block diagram illustrating a second temperature control part shown in FIG. 1.

Referring to FIGS. 1 to 6, the second temperature control part 150 includes an auxiliary information processing part 153 and a heat control part 154.

The auxiliary information processing part 152 applies the temperature control signal received from the CPU 110 to the heat control part 154.

The heat control part 154 controls the temperature of the PCR module 200 based on the temperature control signal received from the auxiliary information processing part 152. In the embodiment of the present invention, the heat control part 154 includes a temperature sensor 154a and a fan 154b. The temperature sensor 154a senses the temperature of the PCR module 200 to transmit the sensed temperature to the auxiliary information processing part 152. The fan 154b heats or cools the PCR module 200 based on the temperature control signal.

In another embodiment of the present invention, the heat control part 154 may not include the temperature sensor 154a and the fan 154b, but may include a thermoelectric element (not shown). In still another embodiment of the present invention, the heat control part 154 may include a water cooling fan (not shown).

The PCR module 200 amplifies genetic material included in the specimen and monitors an amount of the amplified genetic material in real time to transmit a photo sensing signal to the read system 100. In the embodiment of the present invention, the PCR module 200 transmit the temperature signal to the reader system 100.

In the embodiment of the present invention, the PCR module 200 includes a control interface 210, a reaction container 240, a photo sensor 250, a temperature sensor 260, and a first temperature control part 270. For example, the PCR module 200 may be a replaceable module having a predetermined specimen, and may be disposable after being once used. In another embodiment of the present invention, the PCR module 200 may include a light source driving part 220 and a light source 230.

In the embodiment of the present invention, the control interface 210 may receive a temperature control signal from the reader system 100 to transmit the received temperature control signal to the first temperature control part 270. Also, the control interface 210 receives a photo sensing signal generated from the photo sensor 250 and a temperature signal generated from the temperature sensor 260 to transmit the received photo sensing signal and the temperature signal to the reader system 100.

The reaction container 240 receives the specimen and amplifies the genetic material included in the specimen. In the embodiment of the present invention, the reaction container 240 may include one receiving space or a plurality of receiving spaces. When the reaction container 240 includes the plurality of receiving spaces, one specimen or a plurality of specimens may be simultaneously inspected.

The reaction container 240 may include various materials such as silicon, plastic, etc.

The photo sensor 250 is disposed adjacent to the reaction container 240 to sense luminance of emission light generated from the specimen disposed in the reaction container 240 using a light generated from the light source 230 and having passed through a light source filter 233. For example, the emission light may include fluorescence, phosphorescence, etc. The luminance of the emission light sensed by the photo sensor 250 is transformed into a photo sensing signal, so that the photo sensing signal is applied to the control interface 210.

The temperature sensor 260 is disposed adjacent to the reaction container 240 to represent the temperature of the specimen disposed in the reaction container 240. The temperature sensed by the temperature sensor 260 is transformed into the temperature signal, so that the temperature signal is applied to the control interface 210.

The first temperature control part 270 is disposed to make contact with the reaction container 240 to control the temperature of the reaction container 240. In the embodiment of the present invention, the first temperature control part 270 receives the temperature control signal from the control interface 210 to maintain the temperature of the reaction container 240 at a constant temperature, or heats or cools the reaction container 240. For example, the first temperature control part 270 may include a heater, a thermoelectric element, a cooler, or a combination thereof.

In the embodiment of the present invention, the first temperature control part 270 may increase the temperature of the reaction container 240, and the second temperature control part 150 may decrease the temperature of the reaction container 240. In another embodiment of the present invention, the first temperature control part 270 and the second temperature control part 150 may be integrally formed.

In the embodiment of the present invention, a material having high thermal conductivity may be interposed between the temperature sensor 260 and the reaction container 240 and between the first temperature control part 270 and the reaction container 240 so that heat may be easily transmitted. For example, various materials such as silicon, glass, metal, metal oxide, synthetic resin, etc., may be included between the temperature sensor 260 and the reaction container 240 and between the first temperature control part 270 and the reaction container 240.

In the embodiment of the present invention, the light source 230, the photo sensor 250, the temperature sensor 260, the first temperature control part 270, and the reaction container 240 may have various combinations. For example, the light source 230 may be disposed on one side of the reaction container 240 and the photo sensor 250 may be disposed on the other side of the reaction container 240. When the light source 230 and the photo sensor 250 are disposed on the same side, a luminance caused by the light source 230 instead of a real luminance of the reaction container 240. Thus, the light source 230 is disposed on a different side from the photo sensor 250.

The first temperature control part 270 may be disposed on the same surface as the photo sensor 250. When the temperature sensor 260 and the first temperature control part 270 are disposed on the same side, a temperature of the first temperature control part 270 instead of the real temperature of the reaction container 240 may be sensed. Thus, the temperature sensor 260 and the first temperature control part 270 are disposed on different sides from each other.

In the embodiment of the present invention, a complex temperature sensor system including the temperature sensor 260 of the PCR module 200 and the temperature sensor 154a of the reader system 100 may be used. In another embodiment of the present invention, only the temperature sensor 260 may be included in the PCR module 200 and integrally formed with the photo sensor 250. In still another embodiment of the present invention, a photo sensor (not shown) may be integrally formed with the second temperature control part 150.

Figure 7:
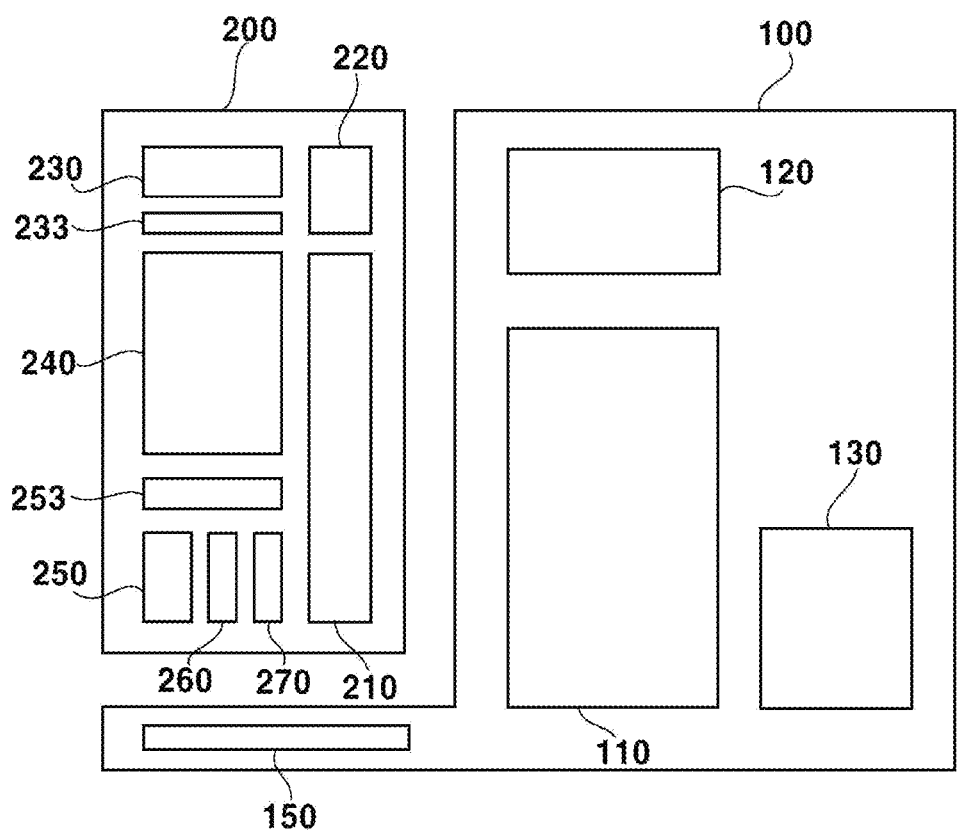
FIG. 7 is a block diagram illustrating a read system for a PCR module according to another embodiment of the present invention.

FIG. 7 is a block diagram illustrating a read system for a PCR module according to another embodiment of the present invention. The reader system for the PCR module of FIG. 7 is substantially the same as shown in FIGS. 1 to 6 except a light source and a light source driving part, and thus, any repetitive explanation concerning the above elements will be omitted.

Referring to FIG. 7, the reader system 100 for the PCR module is detachably combined with the PCR module 200 and operates the PCR module 200.

The reader system 100 includes a central processing unit (CPU) 110, a memory 120, an interface 130, and a second temperature control part 159.

The PCT module 200 includes a control interface 210, a light source 230, a light source filter 233, a reaction container 240, a photo sensor 250, a temperature sensor 260, and a first temperature control part 270. The PCR module 200 may be a replaceable module having a predetermined specimen, and may be disposable after being once used.

Figure 8:
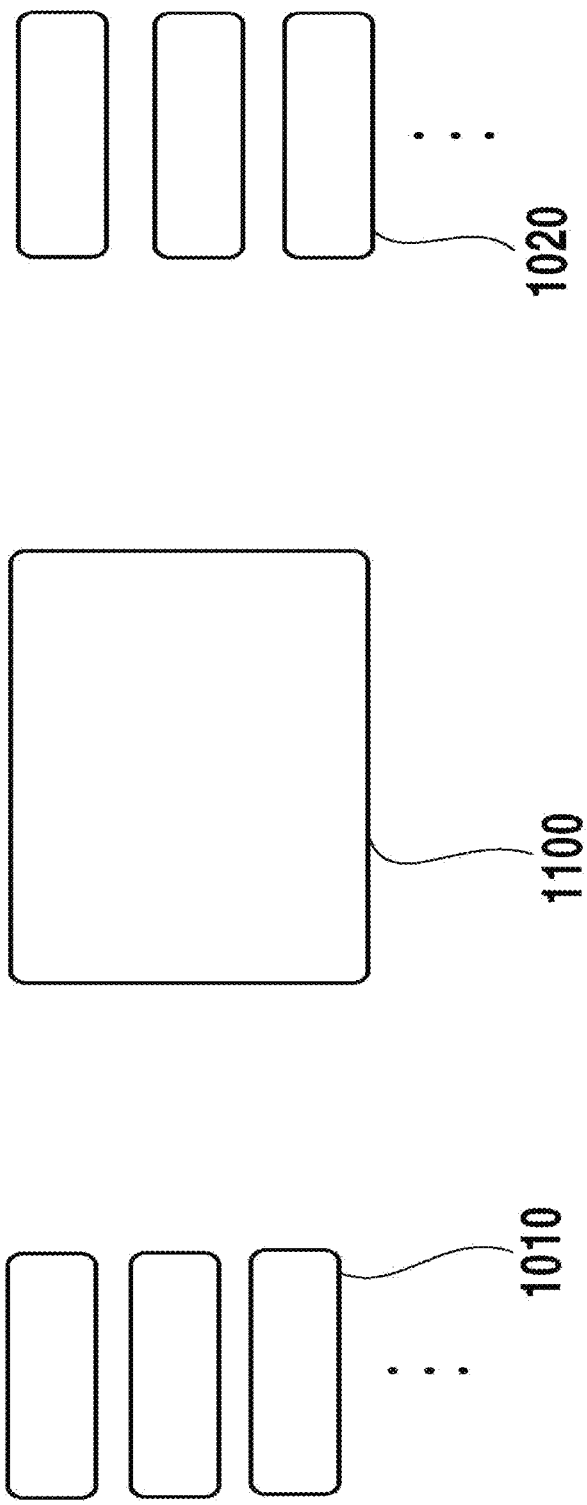
FIG. 8 is a block diagram illustrating a method of inspecting according to one embodiment of the present invention.
Figure 9:
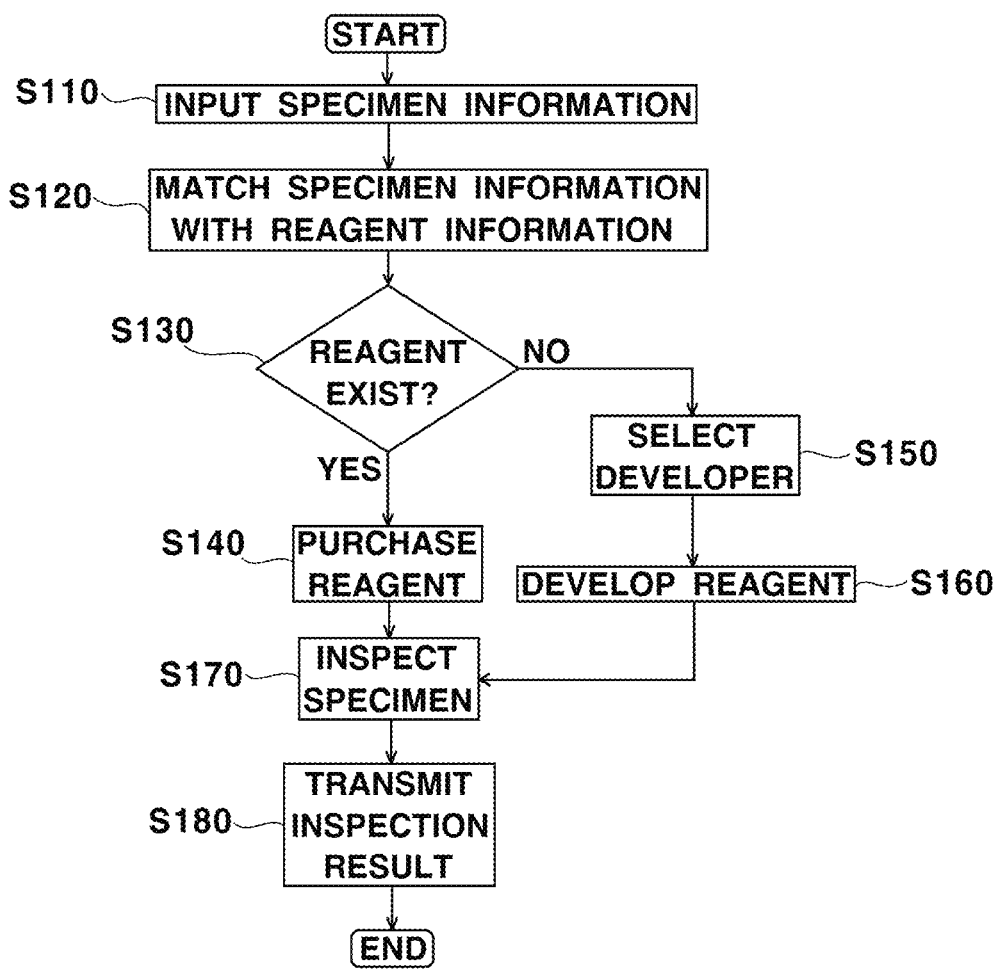
FIG. 9 is a flow chart illustrating the method of inspecting shown in FIG. 8.

FIG. 8 is a block diagram illustrating a method of inspecting according to one embodiment of the present invention. FIG. 9 is a flow chart illustrating the method of inspecting shown in FIG. 8. A reader system and a PCR module of FIG. 8 is substantially the same as shown in FIGS. 1 to 7, and thus, any repetitive explanation concerning the above elements will be omitted.

Referring to FIGS. 2, 8, and 9, firstly specimen information is input through a user terminal 1200 (step S110). The specimen information input by the user terminal 1200 is transmitted to a central processing server 1000 through a communication network such as an internet and/or the like. For example, the user terminal 1200 includes terminals of various shapes such as a smartphone, a personal computer, etc., which are capable of wire/wireless communication.

Then, the central processing server 1000 matches the specimen information input from the user terminal 1200 with previously stored reagent information (step S120).

Then, existence of reagent matching the input specimen information among the previously stored reagent information is checked (step S130).

When the reagent matching the input specimen information among the previously stored reagent information exists, information of purchasing corresponding reagent to reagent developer's terminal 1100 (step S140).

When the reagent matching the input specimen information among the previously stored reagent information does not exist, information of selecting a developer is transmitted to a plurality of reagent developer's terminals 1100, and a developer of the corresponding reagent is selected through information responsive to the reagent developer's terminal 1100 (step S150). Then, the reagent is developed (step S160).

Then, the specimen is inspected using the reader system 100 and the PCR module 200 shown in FIGS. 1 to 7 (step S170). In the embodiment of the present invention, the PCR module 200 is provided in a state of including the reagent supplied by the reagent developer. The specimen provided by the user is injected into the PCR module 200 including the reagent, and then, the PCR module 200 is mounted in the reader system 100 and analyzed. In the embodiment of the present invention, the reader system 100 may be small-sized, so that the reader system 100 may be integrally formed with the user terminal 1200.

Then, the result of inspection is transmitted to the central processing server 1000 and/or the user terminal 1200 (step S180).

Figure 10:
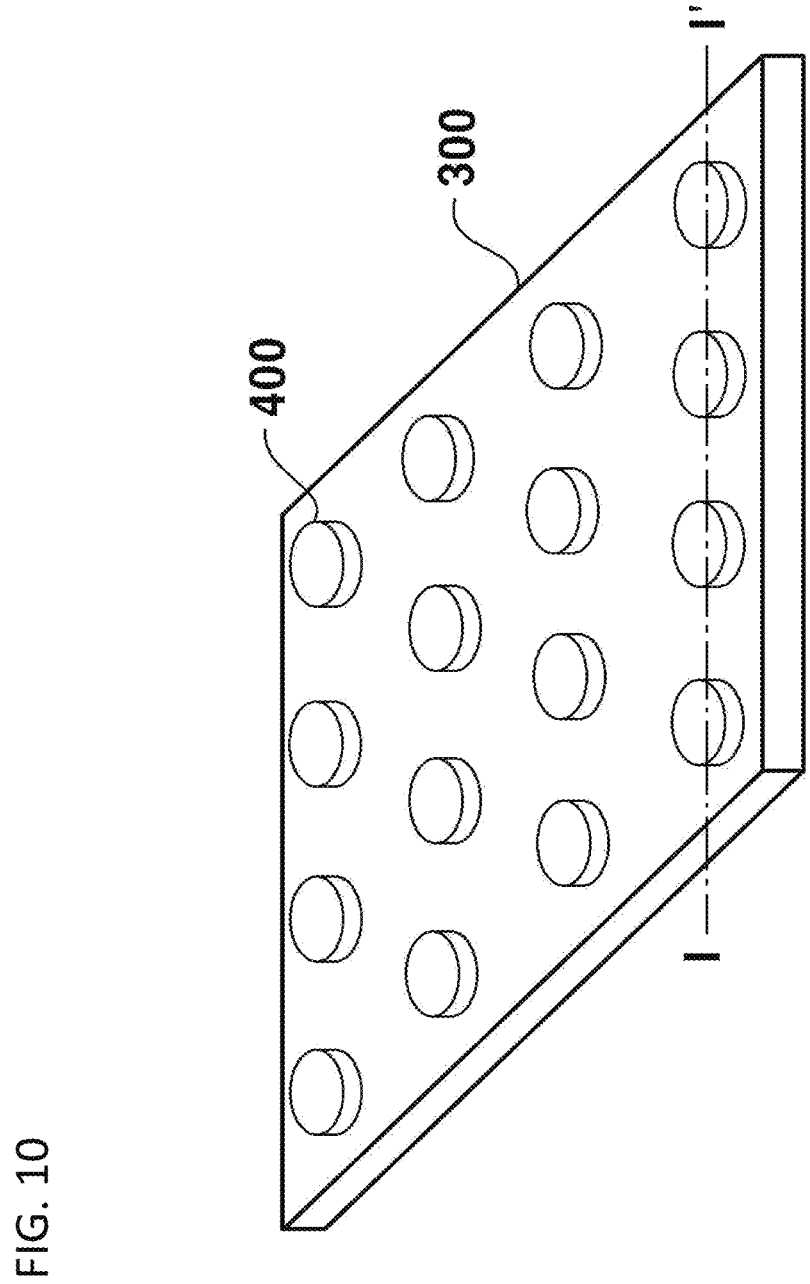
FIG. 10 is a perspective view illustrating a PCR module according to one embodiment of the present invention.
Figure 11:
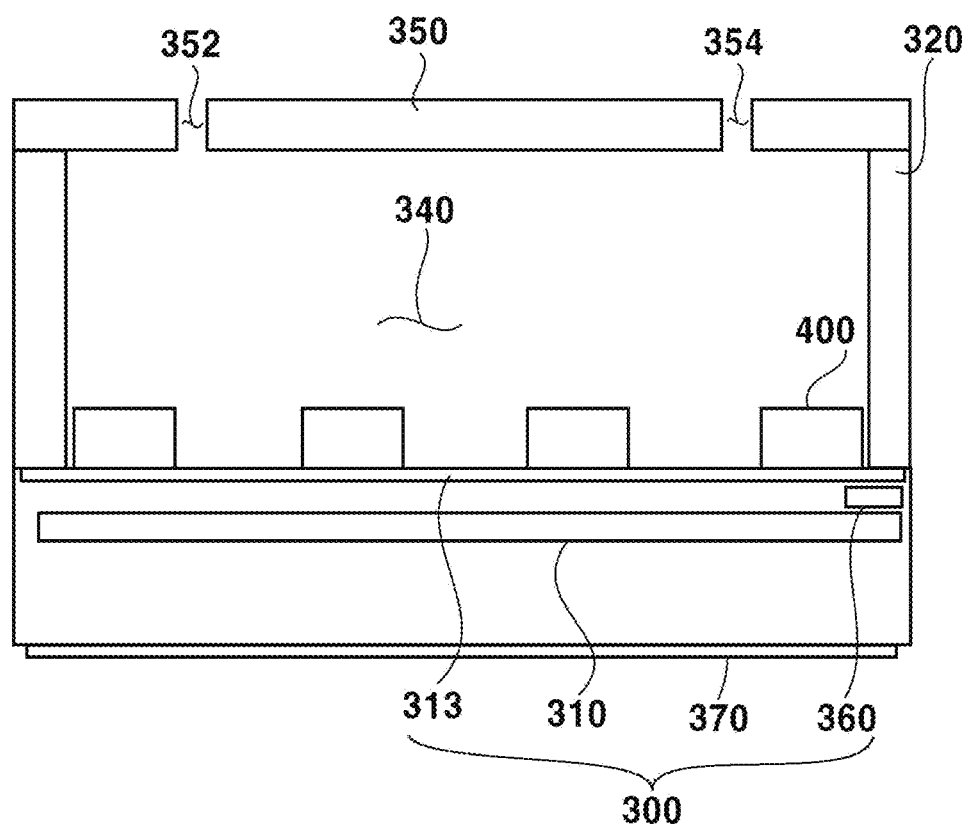
FIG. 11 is a cross-sectional view taken along a line I-I' of FIG. 10.

FIG. 10 is a perspective view illustrating a PCR module according to one embodiment of the present invention. FIG. 11 is a cross-sectional view taken along a line I-I' of FIG. 10. The PCR module of FIG. 10 is substantially the same as shown in FIGS. 1 to 9, and thus, any repetitive explanation concerning the above elements will be omitted. For convenience of explanation, in FIG. 10, a partition wall and a cover are omitted.

Referring to FIGS. 10 and 11, the PCR module includes a photo sensor assembly 300, a 3-dimensional (3D) organic pad, a partition wall 320, and a cover 350. In the embodiment of the present invention, the 3D organic pad is a pad capable of 3-dimensaionally amplifying a specimen including organic material, and may include a hydrogel pad 400, a spin on glass (SOG) pad, etc.

The photo sensor assembly 300 includes a photo sensor array 310, a fluorescent filter 313, a first temperature control part 370, and a temperature sensor 360. The photo sensor array 310 includes a plurality of photo sensors arranged in an array shape. For example, the photo sensor array 310 may includes a plurality of photo diodes, a plurality of thin film transistors, etc.

The fluorescent filter 313 is disposed on the photo sensor array 310 to filter noise of an external light, light generated from a light source, etc., and transmit only fluorescent light generated from the specimen.

The hydrogel pad 400 is disposed on the photo sensor assembly 300 and includes hydrogel. When the hydrogel is mixed with water, the hydrogel is not melted or dissolved but is cross-linked into high polymer chains or polymer chins, thereby maintaining 3-dimensional structure. The hydrogel is hydrophilic material and includes polymer chains forming a plurality of cross-links. For example, the hydrogel may include various kinds of hydrogels such as polyethylene diacrylate (PEGDA) hydrogel, PMA hydrogel, polydimethylamino acrylamide (PDGPA) hydrogel, polyethyloxazoline, silicon hydrogel, etc. In the embodiment of the present invention, the hydrogel pad 400 may include PEGDA hydrogel.

In another embodiment of the present invention, the 3D organic pad may include a pad (not shown) formed using spin on glass (SOG) instead of the hydrogel pad 400.

The hydrogel pad 400 may have various shapes such as a cylindrical disc shape, a quadrangular disc shape, a hexagonal disc shape, a hexahedron shape, a bowl shape, a pillar shape having a recess in a center thereof, a concave lens shape, a convex lens shape, an embossing shape, etc.

In the embodiment of the present invention, the hydrogel pad 400 may be formed through photo patterning using a photo mask and ultraviolet light. In another embodiment of the present invention, a preliminary hydrogel pad (not shown) may be formed through a photo process at the outside, and then, the preliminary hydrogel pad is introduced onto the photo sensor assembly 300, so that the hydrogel pad 400 may be combined. For example, the preliminary hydrogel pad (not shown) may flow a space on the photo sensor assembly 300 with fluid, so that the hydrogel pad 400 may be sequentially dropped. In another embodiment of the present invention, various methods such as printing, detachably combining, etc., may be used.

The hydrogel pad 400 includes a primer and a DNA probe. The primer is a small DNA attached to an area adjacent to gene nucleotide sequence to be amplified, and is a starting DNA when polymerase amplifies DNA. The DNA probe is a DNA part of short length, and is combined with a predetermined DNA to inspect the predetermined DNA. In another embodiment of the present invention, a DNA chip may be used instead of the hydrogel pad 400.

In the embodiment of the present invention, the PCR module may include a plurality of hydrogel pads 400, and different primers may be disposed on the hydrogel pads 400. Thus, multi genotypes may be inspected. In the embodiment of the present invention, the same primers are disposed along the same column, and when the column is changed, different primer is disposed. Thus, a plurality of data inspected in the same column are compared to ensure credibility of the inspection result.

Also, in a conventional multi inspection, wavelengths of fluorescent lights are different, and thus, a structure of optical member may be complex. However, in the embodiment of the present invention, different primers are disposed on different hydrogel pads 400, so that multi inspection may be performed although a single fluorescent material is used, thereby simplifying a structure of the photo sensor assembly 300.

Also, a conventional array type includes genetic material disposed only on a surface thereof, so that gene amplification speed is very slow. However, the hydrogel pad 400 has 3-dimensional structure of the polymer chains, and gene amplification is also performed in the hydrogel pad 400, so that gene amplification speed is very fast. Thus, an array may be formed by the hydrogel pads 400, so that gene amplification may be performed in real time at various positions. Also, fluorescent light is only generated from the hydrogel pad 400, so that amount of light is increased to increase intensity of a signal, thereby realizing more sensitive test.

The partition wall 320 is extended from sides of the photo sensor assembly 300 to form the reaction container 340. The partition wall 320 may include various materials such as plastic, PDMS, silicon, metal, etc.

The cover 350 covers an upper portion of the cover 320. An let 352 and an outlet 354 are formed in the cover 350. The specimen (not shown) is introduced into the reaction container 340 through the inlet 352, and the specimen (not shown) may be discharged to the outside through the outlet 354 after reaction is finished.

FIGS. 12 to 15 are cross-sectional views illustrating a method of manufacturing the PCR module shown in FIG. 10.

Figure 12:
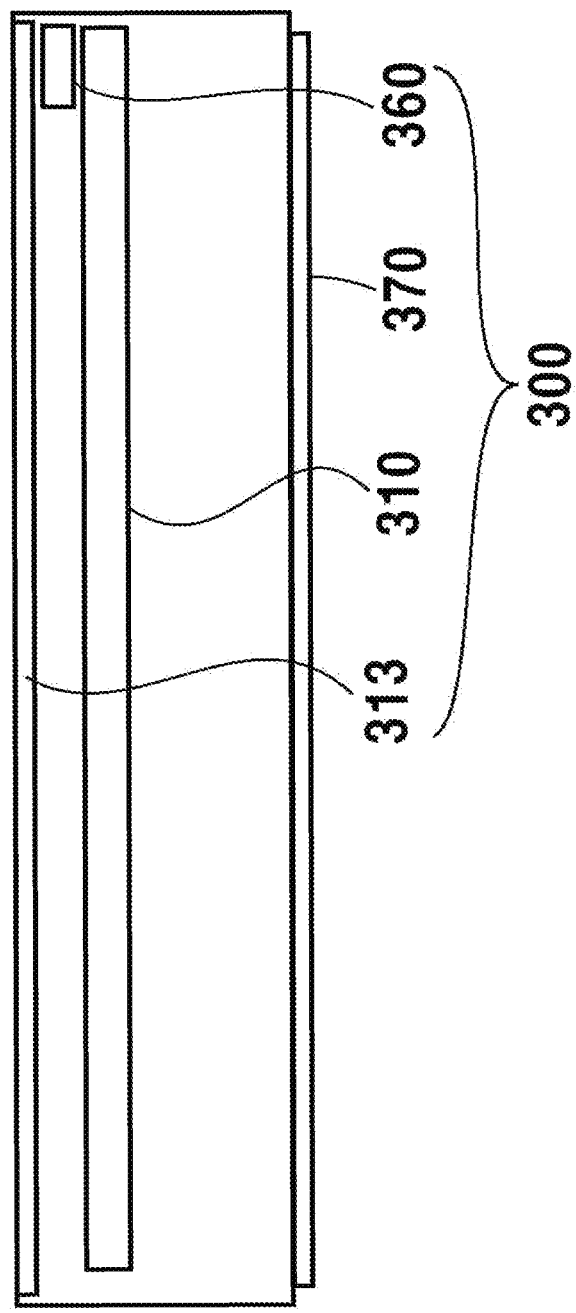
FIGS. 12 to 15 are cross-sectional views illustrating a method of manufacturing the PCR module shown in FIG. 10.

Referring to FIG. 12, firstly the photo sensor assembly 300 is formed. In the embodiment of the present invention, the photo sensor array 310, the temperature sensor 360, and the first temperature control part 370 are formed on a base substrate, and the fluorescent filter 313 is formed thereon. For example, the photo sensor array 310, the temperature sensor 360, and the first temperature control part 370 may be formed through a semiconductor process.

Figure 13:
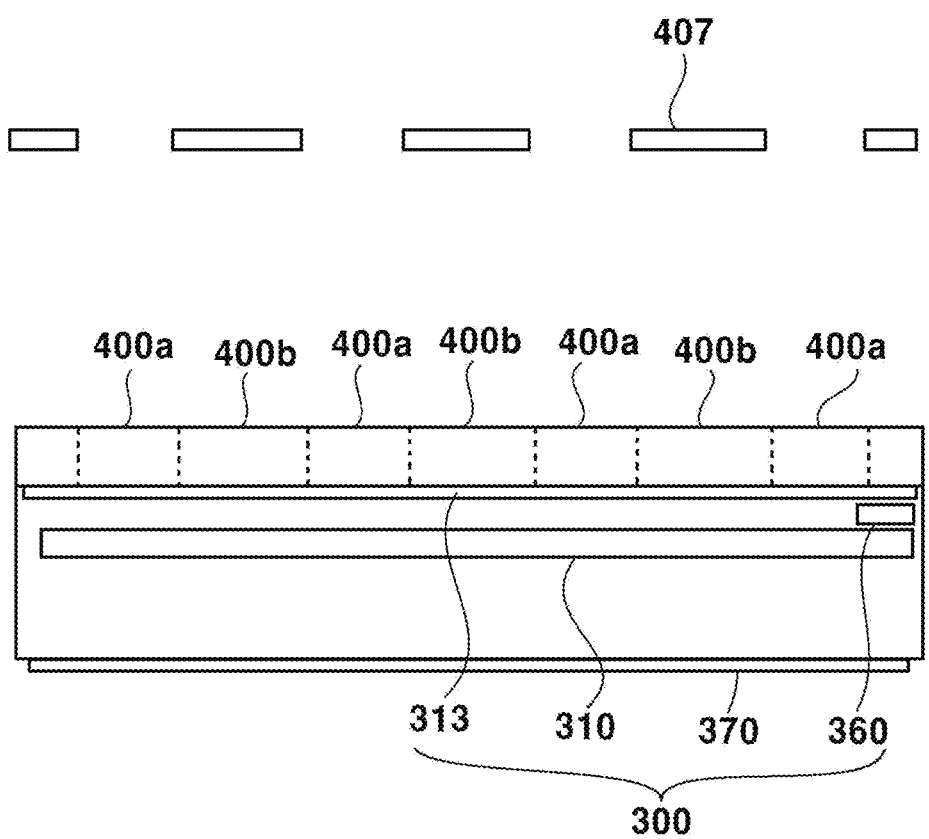

Referring to FIG. 13, hydrogel 400a and 400b is then coated on the photo sensor assembly 300. A portion 400a of the coated hydrogel 400a and 400b is exposed through a mask 407.

Figure 14:
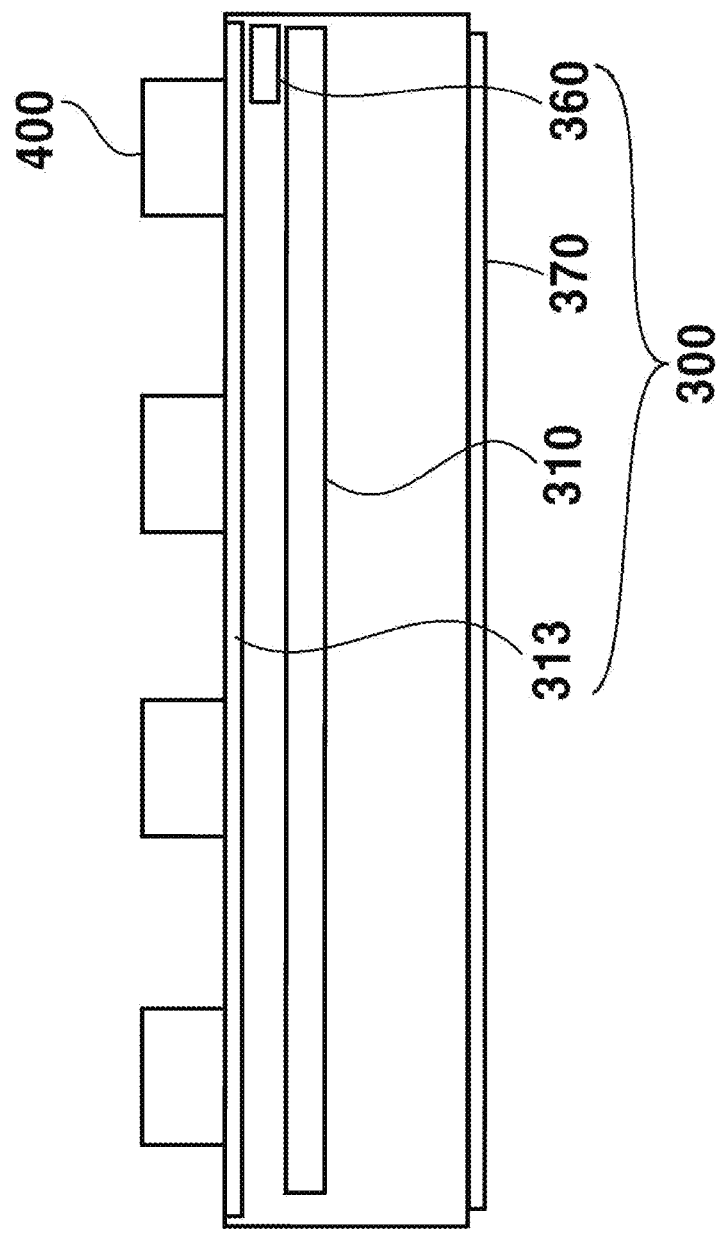

Referring to FIG. 14, the coated hydrogel 400a and 400b is then developed to form the hydrogel pad 400.

Figure 15:
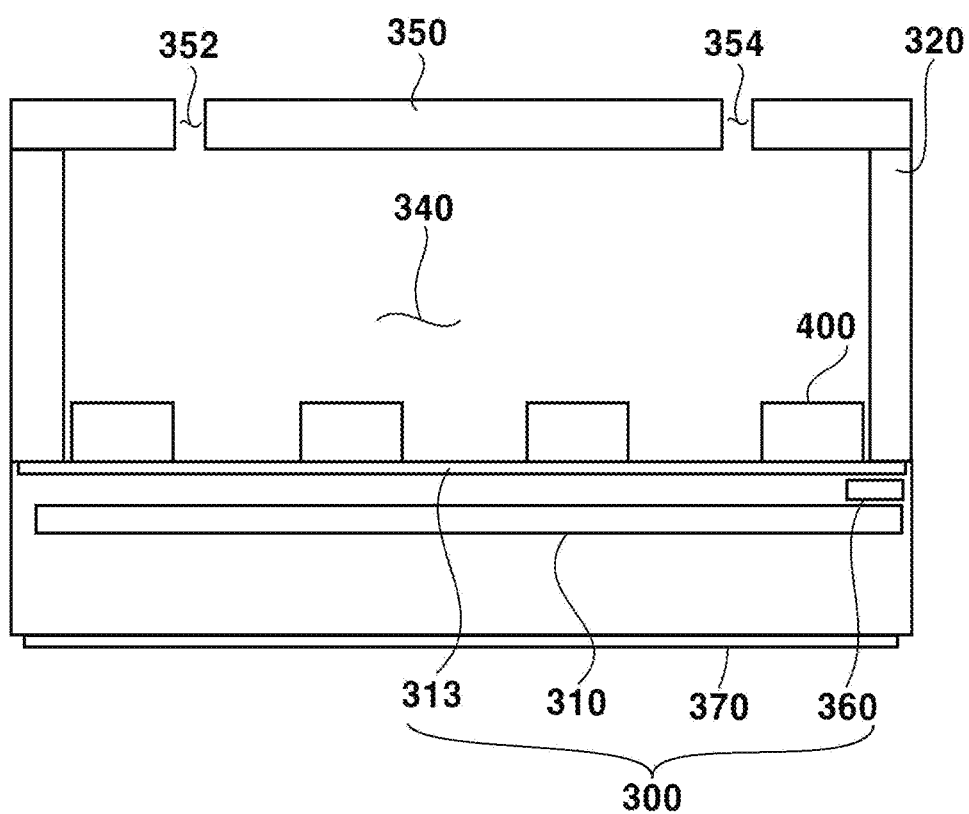

Referring to FIG. 15, the partition wall 320 and the cover 350 are then formed on the photo sensor assembly 300 on which the hydrogel pad 400 is formed.

Figure 16:
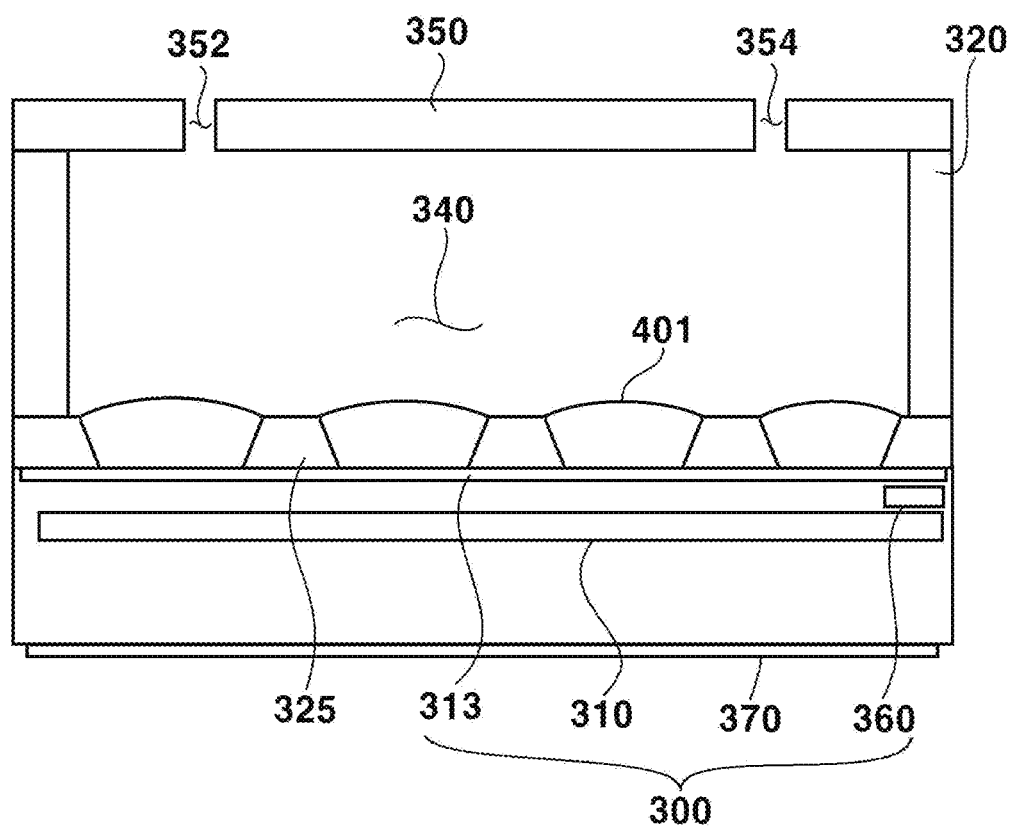
FIG. 16 is a cross-sectional view illustrating a PCR module according to another embodiment of the present invention.

FIG. 16 is a cross-sectional view illustrating a PCR module according to another embodiment of the present invention. The PCR module of FIG. 16 is substantially the same as shown in FIGS. 10 and 11 except a bank, and thus, any repetitive explanation concerning the above elements will be omitted.

Referring to FIG. 16, the PCR module includes a photo sensor assembly 300, a hydrogel pad 401, a partition wall 320, a bank 325, and a cover 350.

The bank 325 is disposed on the photo sensor assembly 300, and forms a plurality of divided spaces in an array shape. The bank 325 may include various materials such as inorganic insulating material, photoresist, plastic, silicon, metal, etc.

The hydrogel pad 401 is disposed in the spaces divided by the banks 325 adjacent to each other on the photo sensor assembly 300. The hydrogel pad 401 may include hydrogel.

The partition wall 320 is extended from sides of the photo sensor assembly 300 on which the bank 325 is formed to form the reaction container 340. The partition wall 320 may include various materials such as silicon, plastic, rubber, polymer, metal, ceramic, PDMS, carbon based material, etc.

FIGS. 17 to 22 are cross-sectional views illustrating a method of manufacturing the PCR module shown in FIG. 16.

Figure 17:
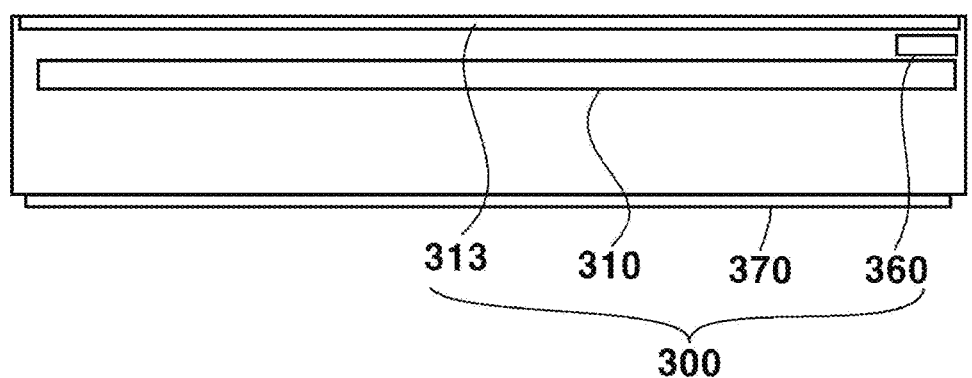
FIGS. 17 to 22 are cross-sectional views illustrating a method of manufacturing the PCR module shown in FIG. 16.

Referring to FIG. 17, firstly, the photo sensor assembly 300 is formed.

Figure 18:
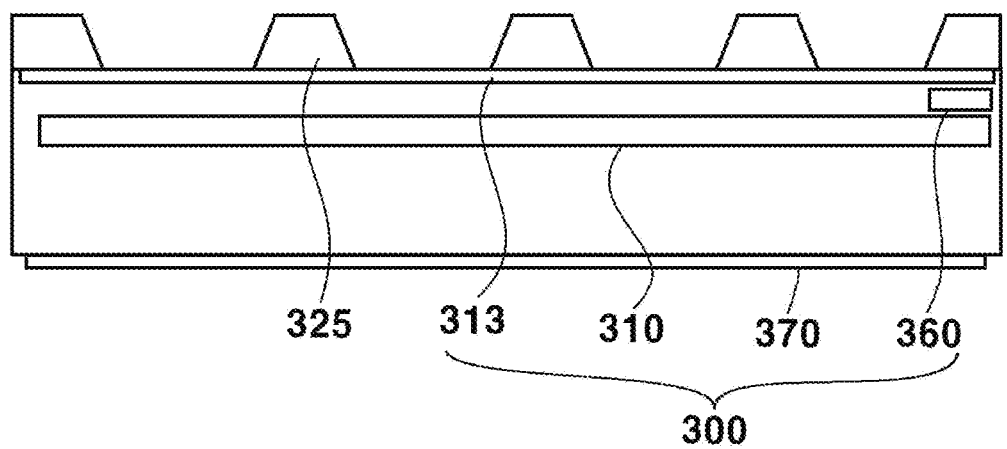

Referring to FIG. 18, the bank 325 is then formed on the photo sensor assembly 300. In the embodiment of the present invention, the bank 325 may be formed in various methods such as photolithography process, printing process, nano-machining process, etc.

Figure 19:
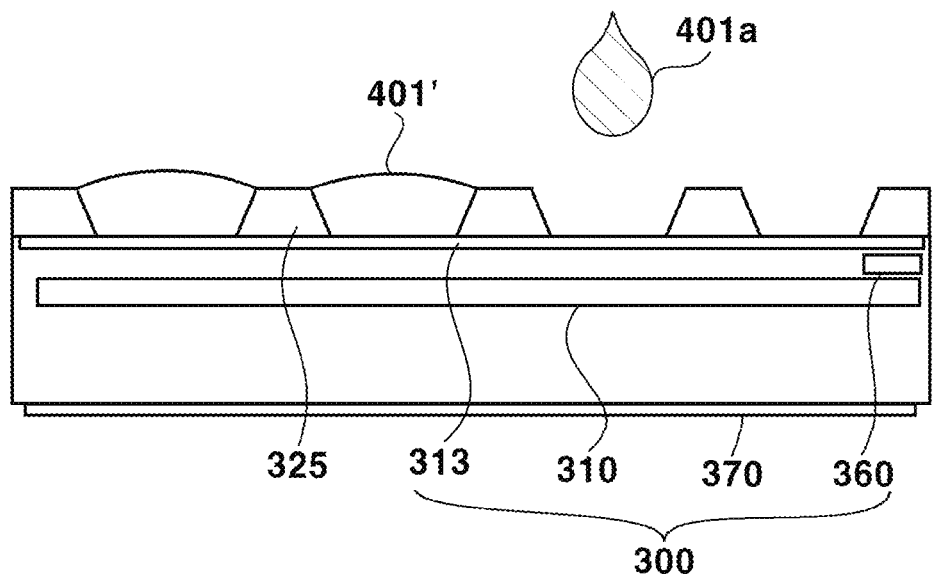

Referring to FIG. 19, hydrogel droplets 401a are dropped in the spaces formed by the banks 325 adjacent to each other. In the embodiment of the present invention, the dropped hydrogel droplet 401' may not be solidified and may have fluidity.

Figure 20:
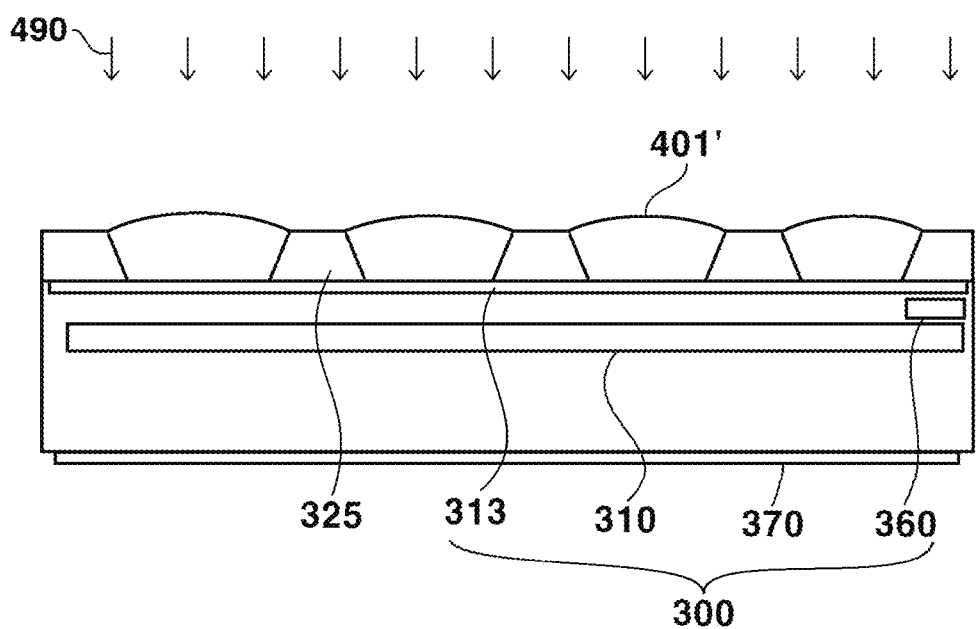
Figure 21:
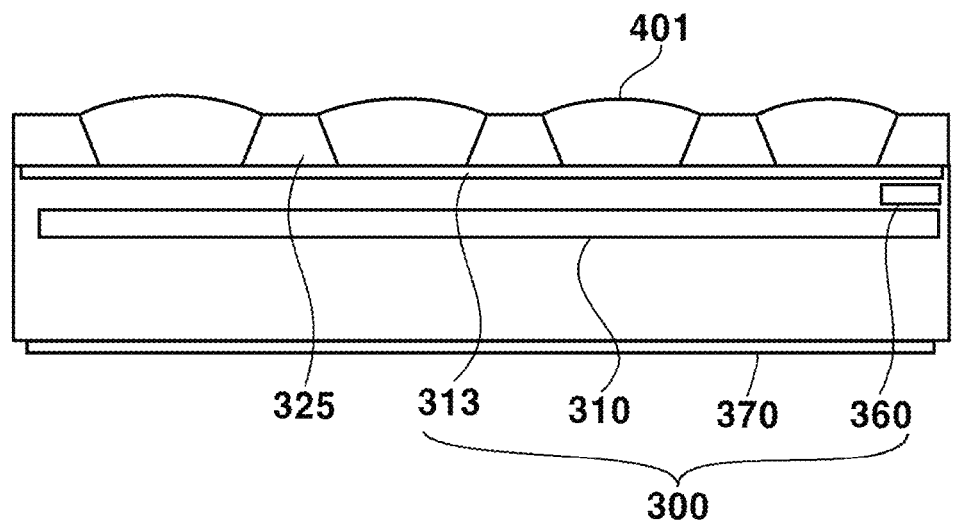

Referring to FIGS. 20 and 21, ultraviolet (UV) 490 is irradiated onto the dropped hydrogel droplet 401' to form the hydrogel pad 401.

Figure 22:
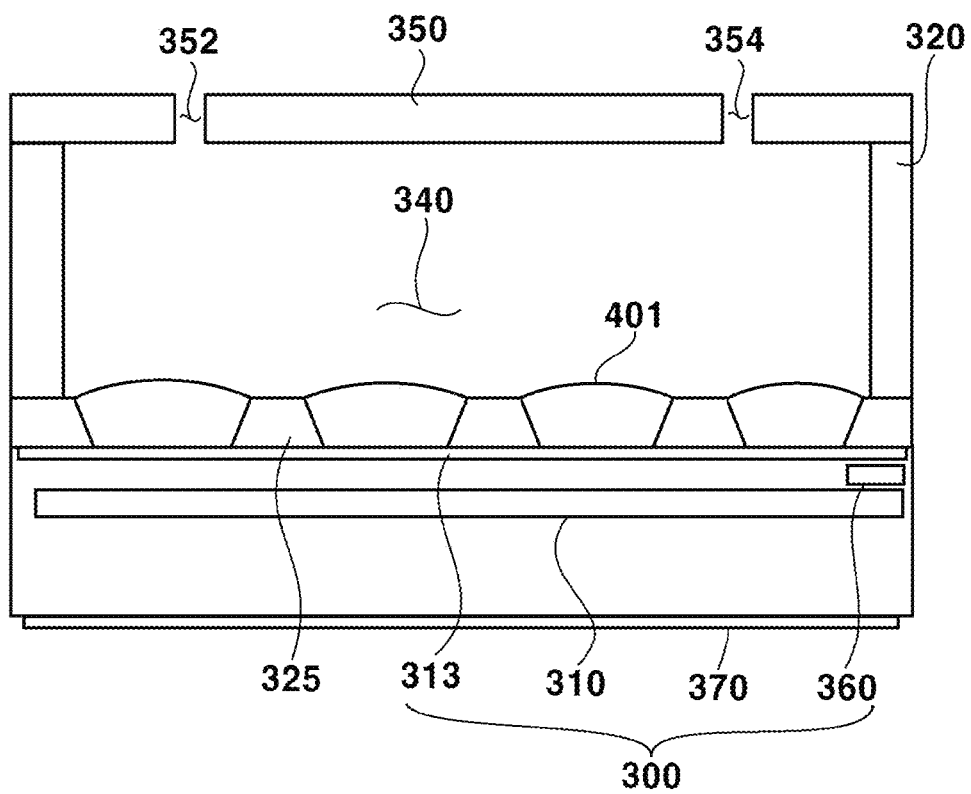

Referring to FIG. 22, the partition wall 320 and the cover 350 are formed on the photo sensor assembly 300 on which the hydrogel pad 401 is formed.

Figure 23:
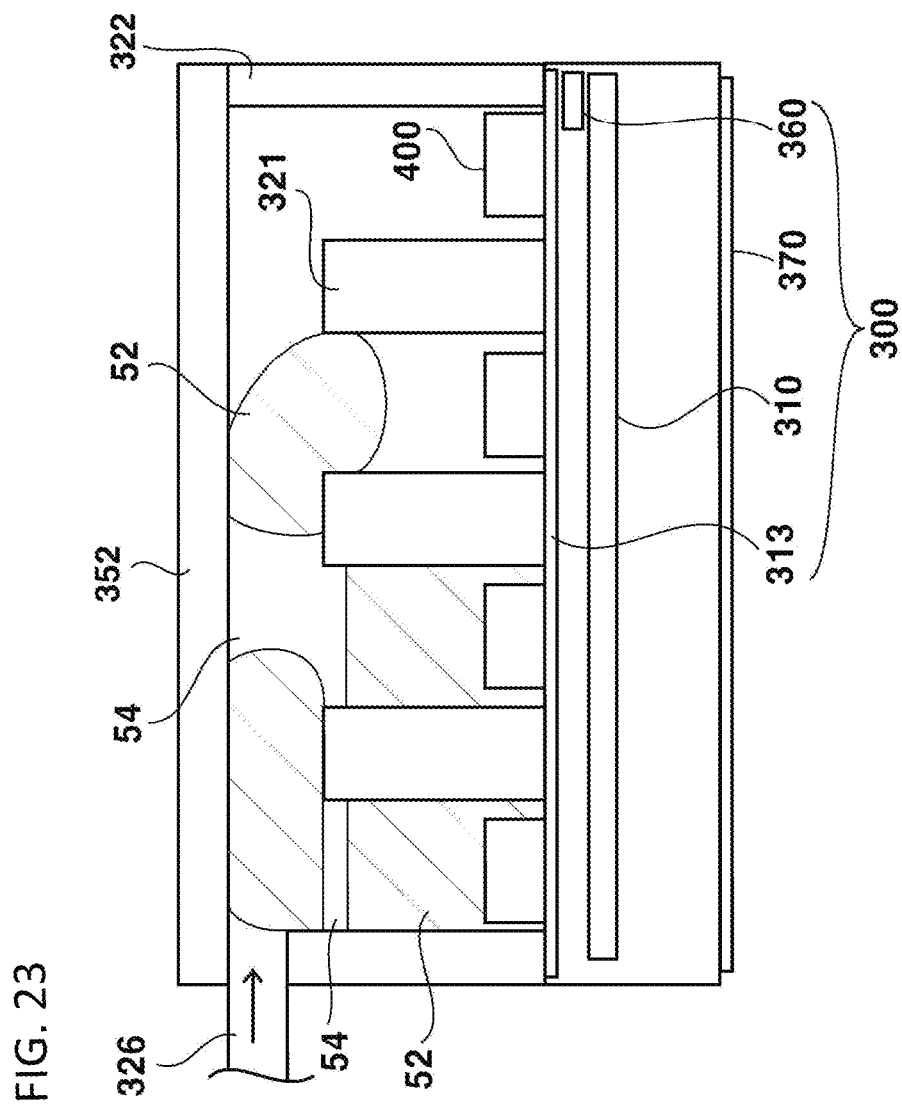
FIG. 23 is a cross-sectional view illustrating a method of inspecting using a PCR module according to still another embodiment of the present invention.

FIG. 23 is a cross-sectional view illustrating a method of inspecting using a PCR module according to still another embodiment of the present invention. The PCR module of FIG. 23 is substantially the same as shown in FIG. 16 except a specimen injection part, a partition wall, a bank, and a cover, and thus, any repetitive explanation concerning the above elements will be omitted.

In the embodiment of the present invention, a height of the bank 321 is protruded greater than that of the hydrogel pad 400, so that the hydrogel pad 400 is received in a space divided by banks 321 adjacent to each other.

The partition wall 322 is protruded from sides of the photo sensor assembly 300, and has an opened side to be connected to the specimen injection part 326.

The cover 352 is connected to an upper surface of the partition wall 322. In the embodiment of the present invention, the height of the partition wall 322 is protruded greater than that of the bank 321 to form a path through which specimens 52a, 52b, 52c, and 52d and a buffering agent 54 between a lower surface of the partition wall 322 and the upper surface of the bank 321.

The buffering agent 54 includes fluid having low reactivity with the specimens 52a, 52b, 52c, and 52d. For example, the buffering agent 54 may include oil, gel, pure water, etc. The buffering agent 54 separates the specimens 52a, 52b, 52c, and 52d, so that the specimens 52a, 52b, 52c, and 52d adjacent to each other may not be mixed.

A method of injecting the specimens 52a, 52b, 52c, and 52d into the PCR module using the specimen injection part 326 is as follows.

Firstly, the specimens 52a, 52b, 52c, and 52d and the buffering agent 54 are alternately disposed in the specimen injection part 326.

Then, when a pressure is applied to one side of the specimen injection part 326, a first specimen 52a disposed in the specimen injection part 326 is transported in a direction toward the partition wall 322.

Then, when the pressure is continuously applied to the one side of the specimen injection part 326, the first specimen 52a in the specimen injection part 326 passes through the partition wall 322. The first specimen 52a having passed through the partition wall 322 flows downwardly by dead load, and is dropped in a space formed between the bank 321 and the partition wall 322, thereby covering the hydrogel pad 400.

Then, when the pressure is continuously applied to the one side of the specimen injection part 326, the buffering agent disposed between the first and second specimens 52a and 52b fills the space between the bank 321 and the partition wall 322.

Then, when the pressure is continuously applied to the one side of the specimen injection part 326, a second specimen 52b sequentially passes through the partition wall 322, the space between the partition wall 322 and the bank 321, and a bank 321 adjacent to the partition wall 322.

Then, when the pressure is continuously applied to the one side of the specimen injection part 326, the second specimen 52b is dropped in a space between adjacent banks 321, thereby covering a second hydrogel 400.

In the same method, when the pressure is continuously applied to the one side of the specimen injection part 326, the second specimen 52b, the buffering agent 54, a third specimen 52c, a buffering agent 54, and a fourth specimen 52d sequentially fill the spaces formed by the adjacent banks 321.

According to the embodiment of the present invention, the specimens 52a, 52b, 52c, and 52d and the buffering agent 54 are alternately disposed in the specimen injection part 326, so that the specimens 52a, 52b, 52c, and 52d may be sequentially injected onto the plurality of hydrogel pads 400 by the simple operation of applying the pressure to the one side of the specimen injection part 326.

Figure 24:
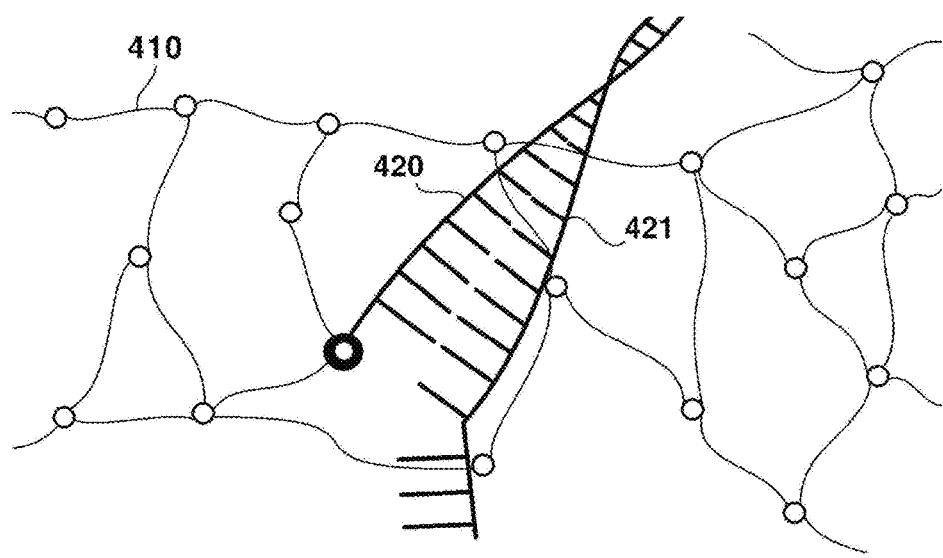
FIG. 24 is an enlarged cross-sectional view illustrating a hydrogel pad used in a method of inspecting using a PCR module according to one embodiment of the present invention.

FIG. 24 is an enlarged cross-sectional view illustrating a hydrogel pad used in a method of inspecting using a PCR module according to one embodiment of the present invention.

Referring to FIGS. 10 and 24, genetic material 421 to be inspected is dropped on a hydrogel pad 400. The dropped genetic material 421 is 3-dimensionally uniformly distributed in the hydrogel pad 400.

Gene amplification 420 starts in the genetic material 421 by primer in each hydrogel pad 400.

In the embodiment of the present invention, the genetic material 421 is uniformly permeated by the polymer chains 410 of the hydrogel pad 400. The gene amplification 420 of the genes of the genetic material 421 permeated in the hydrogel pad 400 starts by the primer. In the embodiment of the present invention, a temperature control part adjusts temperature of the hydrogel pad 400 for the gene amplification 420.

When light generated from a light source is irradiated onto fluorescent material attached to the amplified gene, a fluorescent material of a predetermined wavelength is emitted from the fluorescent material.

The photo sensor array detects fluorescent light emitted from the fluorescent material to inspect existence of the genes.

Figure 25:
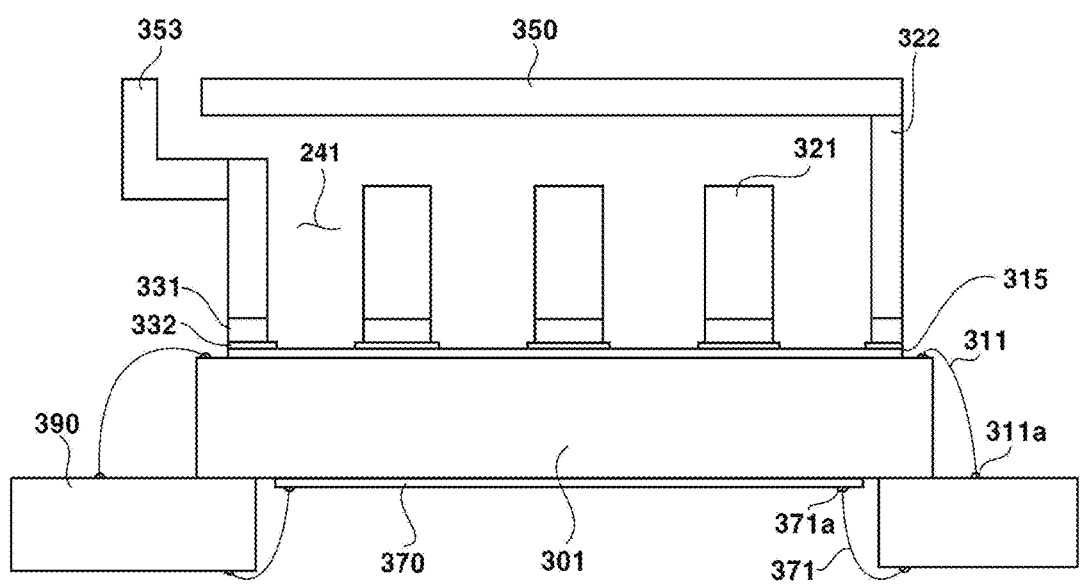
FIG. 25 is a cross-sectional view illustrating a PCR module according to further still another embodiment of the present invention.

FIG. 25 is a cross-sectional view illustrating a PCR module according to further still another embodiment of the present invention. The PCR module of FIG. 25 is substantially the same as shown in FIG. 23 except wires 311 and 317, bondings 311a and 371a, a light source 331, a light blocking pattern 332, a specimen injection part 353, and an interface member 390, and thus, any repetitive explanation concerning the above elements will be omitted.

Referring to FIG. 25, the PCR module includes a photo sensor assembly 301, partition walls 321 and 322, wires 311 and 371, bondings 311a and 371a, an optical filter 315, a light source 331, a light blocking pattern 332, a specimen injection part 353, a cover 350, a first temperature control part 370, and an interface member 390.

The photo sensor assembly 301 includes a photo sensor, a temperature sensor, a driving circuit, etc. In the embodiment of the present invention, the photo sensor assembly 301 may include a first temperature control part.

The partition walls 321 and 322 are protruded from the photo sensor assembly 301 in a vertical direction to form a reaction space 241. In the embodiment of the present invention, the partition walls 321 and 322 may include a partition wall 322 disposed on sides of the photo sensor assembly 301 and a partition wall 321 disposed on a central portion of the photo sensor assembly 301. For example, a height of the partition wall 322 disposed on the sides of the photo sensor assembly 301 may be greater than that of the partition wall 321 disposed in the central portion of the photo sensor assembly 301. When the height of the partition wall 322 disposed on the sides of the photo sensor assembly 301 is greater than that of the partition wall 321 disposed in the central portion of the photo sensor assembly 301, a plurality of specimens may be sequentially injected as shown in FIG. 23.

The optical filter 315 is disposed between the partition walls 321 and 322 and the photo sensor assembly 301 to remove noise and transmit only fluorescent light (or phosphorescent light) generated from the specimen.

The light source 321 irradiates the light into the specimen disposed in the reaction space 241. Material disposed in the specimen generates the fluorescent light or the phosphorescent light using the light generated from the light source 321. The fluorescent light or the phosphorescent light passes through the optical filter 315 to be applied to the photo sensor assembly 301.

In the embodiment of the present invention, the light source 321 is disposed under the partition wall 321. For example, the light blocking pattern 332 is disposed under the light source 321, to prevent direct application of the light generated from the light source 321 to the optical filter 315.

One side of the reaction space 241 is opened, so that the specimen is injected through the specimen injection part 353.

In the embodiment of the present invention, the first temperature control part 370 is formed under the photo sensor assembly 301. In another embodiment of the present invention, the first temperature control part 370 may be variously disposed on an upper portion of the photo sensor assembly 301, an upper portion of the cover 350, a side surface of the partition walls 321 and 322, etc.

The interface member 390 is disposed under the photo sensor assembly 301 to control the photo sensor assembly 301, the light source 321, the first temperature control part 370.

The wires 311 and 371 electrically connect the interface member 380 to the photo sensor assembly 301, the first temperature control part 370, etc. The bondings 311a and 371a are disposed on end portions of the wires 311 and 371 to attach the wires 311 and 371 to the interface member 380, the photo sensor assembly 301, etc. For example, the bondings 311 and 371a may include soldering.

The cover 350 defines an upper portion of the reaction space 241, and may include plastic, polydimethylsiloxane (PDMS), glass, silicon, carbon based material, diamond, metal, high polymer fiber, etc.

Figure 26:
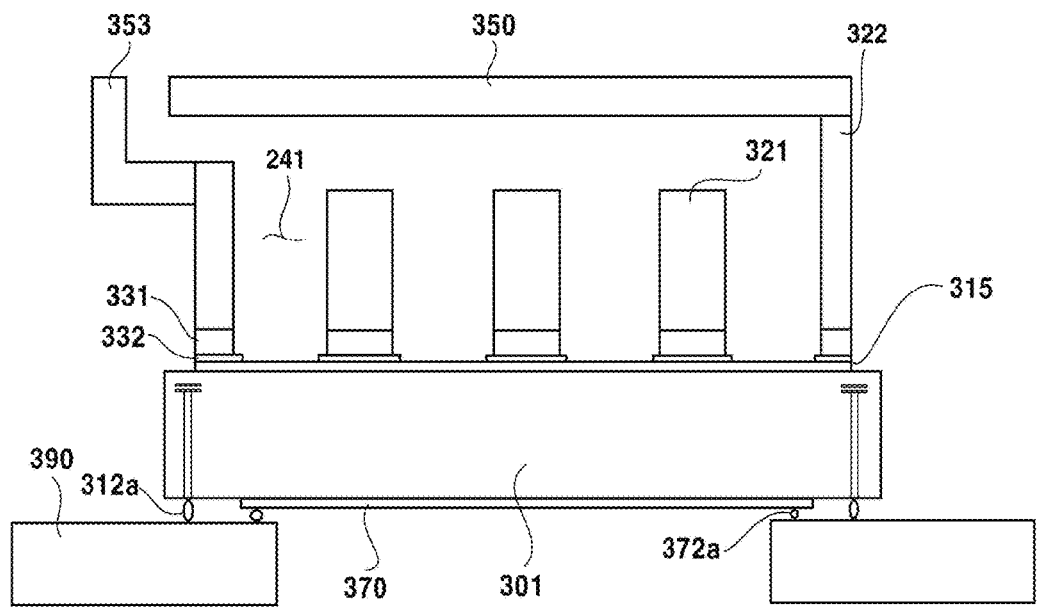
FIG. 26 is a cross-sectional view illustrating a PCR module according to further still another embodiment of the present invention.

FIG. 26 is a cross-sectional view illustrating a PCR module according to further still another embodiment of the present invention. The PCR module of FIG. 26 is substantially the same as shown in FIG. 25 except a through silicon via (TSV) electrode 312 and connecting parts 312a and 372a, and thus, any repetitive explanation concerning the above elements will be omitted.

Referring to FIG. 26, the PCR module includes a photo sensor assembly 301, partition walls 321 and 322, a TSV electrode 312, connecting parts 312a and 372a, an optical filter 315, a light source 331, a light blocking pattern 332, a specimen injection part 353, a cover 350, a first temperature control part 370, and an interface member 390.

The TSV electrode 312 passes through the photo sensor assembly 301 to be electrically connected to an electrode disposed in the photo sensor assembly 301.

The photo sensor assembly 301 is electrically connected to the interface member 390 using the TSV electrode 312 and the connecting parts 312a and 372a. For example, the electrode disposed in the photo sensor assembly 301 may be electrically connected to the interface member 390 through the TSV electrode 312 and the connecting part 312a. The first temperature control part 370 may be electrically connected to the interface member 390 through the connecting part 372a.

In the embodiment of the present invention, a method of combining the interface member 390 to the photo sensor assembly 301 is as follows.

Firstly, the photo sensor assembly 301 including the electrode inside thereof is prepared.

Then, a via hole is formed from a lower portion of the photo sensor assembly 301 is formed to expose a portion of the electrode disposed inside of the photo sensor assembly 301.

Then, conductive material is filled in the via hole to form the TSV electrode 312.

Then the connecting parts 312a and 372a are formed under the photo sensor assembly 301. For example, the connecting parts 312a and 372a may include an anisotropic conductive film, balls and pads, etc.

Then, the interface member 390 is combined from the lower portion of the photo sensor assembly 301.

According to the embodiment of the present invention, additional wire or soldering configured to combine the photo sensor assembly 301 to the interface member 390 may be omitted to decrease defects and improve strength against external impact.

Figure 27:
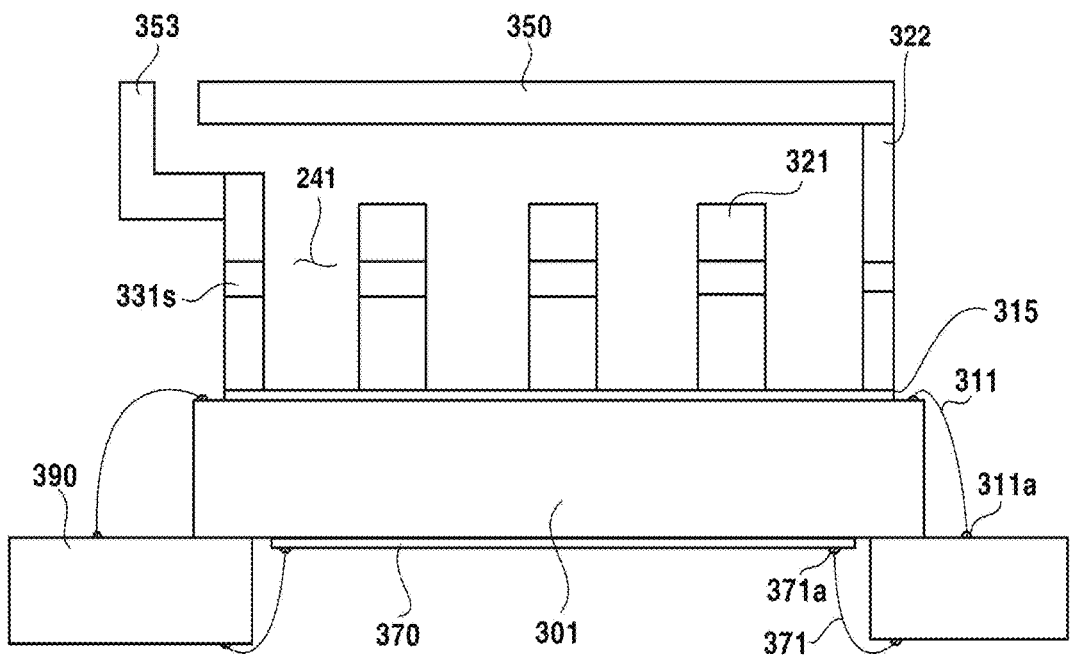
FIG. 27 is a cross-sectional view illustrating a PCR module according to further still another embodiment of the present invention.

FIG. 27 is a cross-sectional view illustrating a PCR module according to further still another embodiment of the present invention. The PCR module of FIG. 27 is substantially the same as shown in FIG. 25 except a light source 331s and a light blocking pattern, and thus, any repetitive explanation concerning the above elements will be omitted.

Referring to FIG. 27, the light sources 331s are disposed on centers of the partition walls 321 and 322 to provide light into the reaction space 241. In the embodiment of the present invention, the light blocking pattern 332 (shown in FIG. 25) may be omitted.

Figure 28:
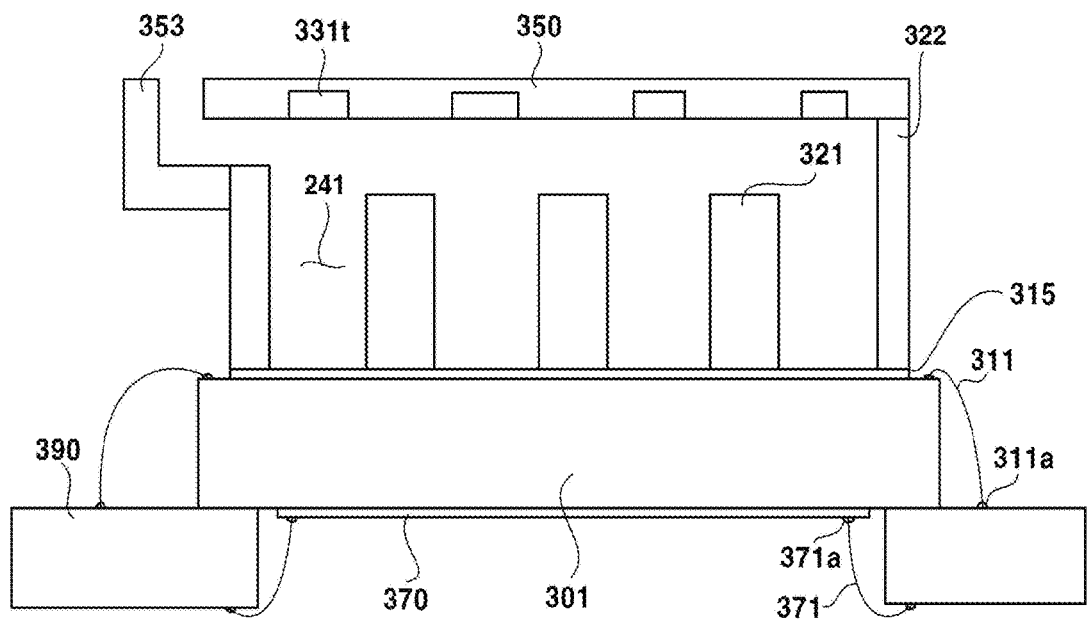
FIG. 28 is a cross-sectional view illustrating a PCR module according to further still another embodiment of the present invention.

FIG. 28 is a cross-sectional view illustrating a PCR module according to further still another embodiment of the present invention. The PCR module of FIG. 28 is substantially the same as shown in FIG. 25 except a light source 331t and a light blocking pattern, and thus, any repetitive explanation concerning the above elements will be omitted.

Referring to FIG. 28, the light source 331t is disposed in a cover 350 to supply light into a reaction space 241. In the embodiment of the present invention, the light blocking pattern 332 (shown in FIG. 25) may be omitted.

Figure 29:
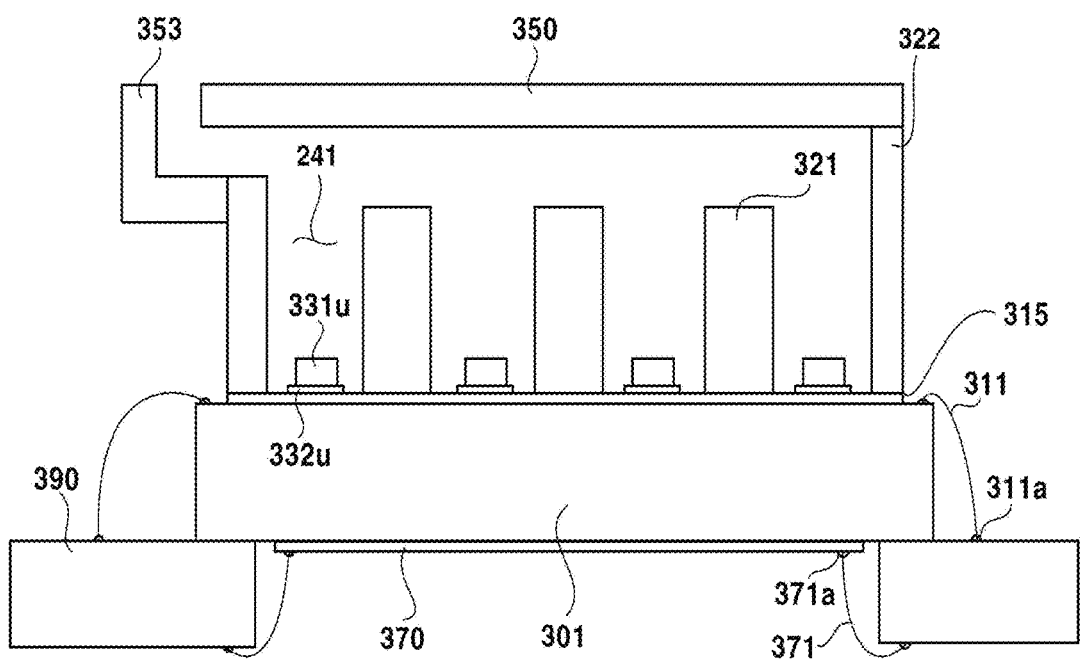
FIG. 29 is a cross-sectional view illustrating a PCR module according to further still another embodiment of the present invention.

FIG. 29 is a cross-sectional view illustrating a PCR module according to further still another embodiment of the present invention. The PCR module of FIG. 29 is substantially the same as shown in FIG. 25 except a light source 331u, and thus, any repetitive explanation concerning the above elements will be omitted.

Referring to FIG. 29, the light source 331u is disposed on a photo sensor assembly 301 to supply light into a reaction space 241. For example, the light source 331u may be disposed on an upper surface of an optical filter 315.

The light blocking pattern 32u is disposed under the light source 331u. For example, the light blocking pattern 332u may be disposed between a lower surface of the light source 331u and an upper surface of the optical filter 315.

Figure 30:
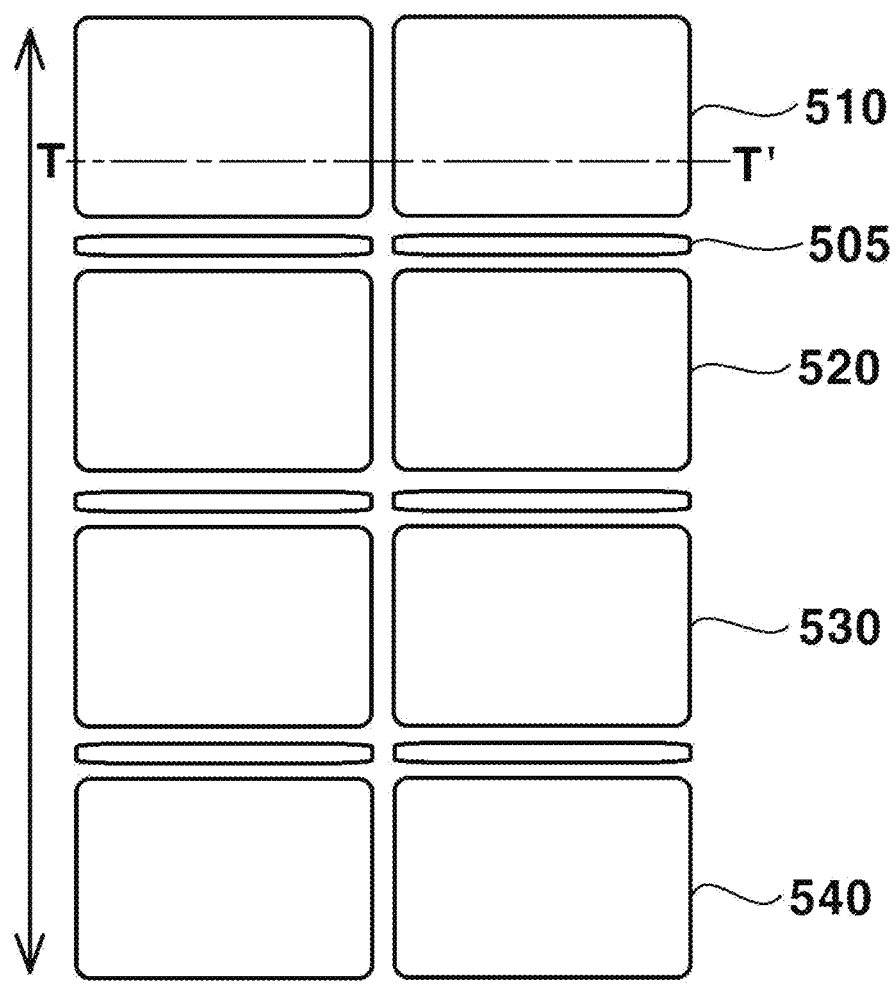
FIG. 30 is a plan view illustrating a thermostatic member according to one embodiment of the present invention.
Figure 31:
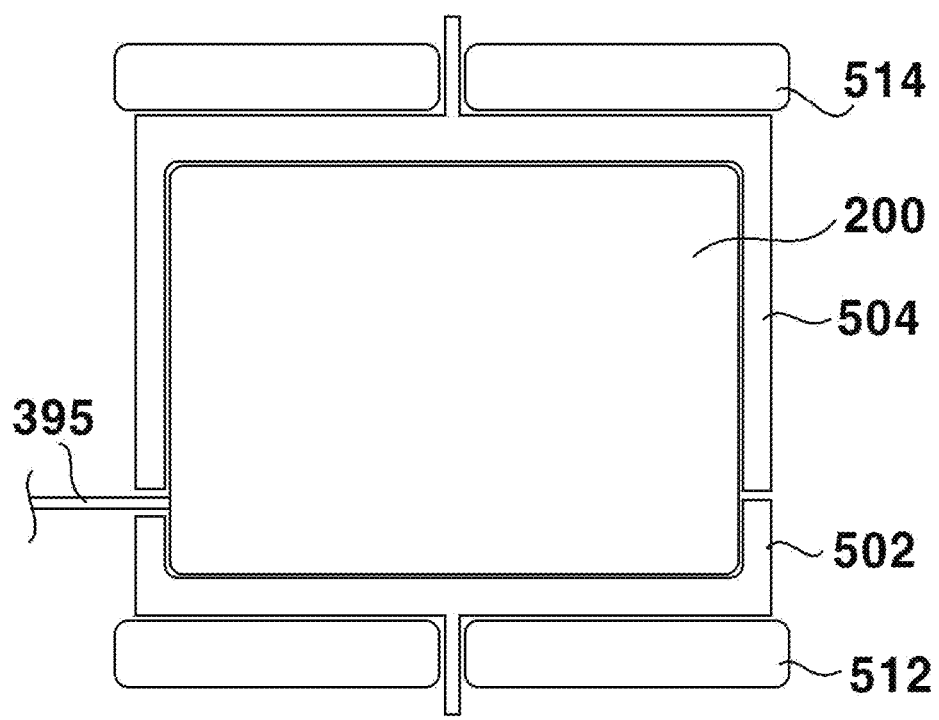
FIG. 31 is a cross-sectional view taken along a line T-T' of FIG. 30.

FIG. 30 is a plan view illustrating a thermostatic member according to one embodiment of the present invention. FIG. 31 is a cross-sectional view taken along a line T-T' of FIG. 30. The PCR module of FIGS. 30 and 31 is substantially the same as shown in FIGS. 1 to 29, and thus, any repetitive explanation concerning the above elements will be omitted.

Referring to FIGS. 30 and 31, the reader system includes a plurality of thermostatic members 510, 520, 530, and 540 and a plurality of heat insulating members 505.

The thermostatic members 510, 520, 530, and 540 are aligned in a straight line and maintain temperatures corresponding stages of PCR cycle. For example, the thermostatic members 510, 520, 530, and 540 may be aligned in various shapes such as a straight line shape, a lattice shape, a curved shape, a circular shape, etc.

In the embodiment of the present invention, a first thermostatic member 510 corresponds to a denaturation stage among the PCR cycle and maintains a temperature of about 92° C. to about 95° C. A second thermostatic member 520 corresponds to a extension stage among the PCR cycle and maintains a temperature of about 72° C. to about 75° C. A third thermostatic member 530 corresponds to an annealing stage among the PCR cycle and maintains a temperature of about 52° C. to about 55° C. A fourth thermostatic member 540 corresponds to a cooling and inspection stage among the PCR cycle and maintains a temperature of about 10 r to about 15° C.

The insulating members 505 is disposed between adjacent thermostatic members 510, 520, 530, and 540 to prevent heat exchange between the adjacent thermostatic members 510, 520, 530, and 540.

In the embodiment of the present invention, each of the thermostatic members 510 includes a plurality of thermostatic parts 512 and 514. For example, the first thermostatic member 510 includes a first thermostatic part 512 disposed under the PCR module 200 and a second thermostatic part 514 disposed on the PCR module 200.

The PCR module 200 is surrounded by a first heat conducting part 502 and a second heat conducting part 504 to exchange heat with each of the thermostatic members 510, 520, 530, and 540. For example, a lower portion of the PCR module 200 may be surrounded by the first heat conducting part 502, and an upper portion of the PCR module 200 may be surrounded by the second heat conducting part 504.

The PCR module 200 surrounded by the first and second heat conducting parts 502 and 504 is transported between the thermostatic members 510, 520, 530, and 540 corresponding to the stages of the PCR cycle, thereby performing the PCR cycle.

For example, a flexible circuit board 395 is disposed in a space between the first heat conducting part 502 and the second heat conducting part 504, so that a driving signal, a photo sensing signal, a temperature signal, etc., of the PCR module 200 may be transmitted through the flexible circuit board 395.

In the embodiment of the present invention, the thermostatic members 510, 520, 530, and 540 configured to maintain different temperatures are used, but the above is an example and various methods may be used. In another embodiment of the present invention, instead of the thermostatic members, air cooling method using a fan, an air compressor, etc., a method of cooling or heating by fluid such as water, oil, etc., a method of cooling by spraying volatile liquid such as water, alcohol, etc., or a method using a thermoelectric element such as Peltier, etc.

Figure 32:
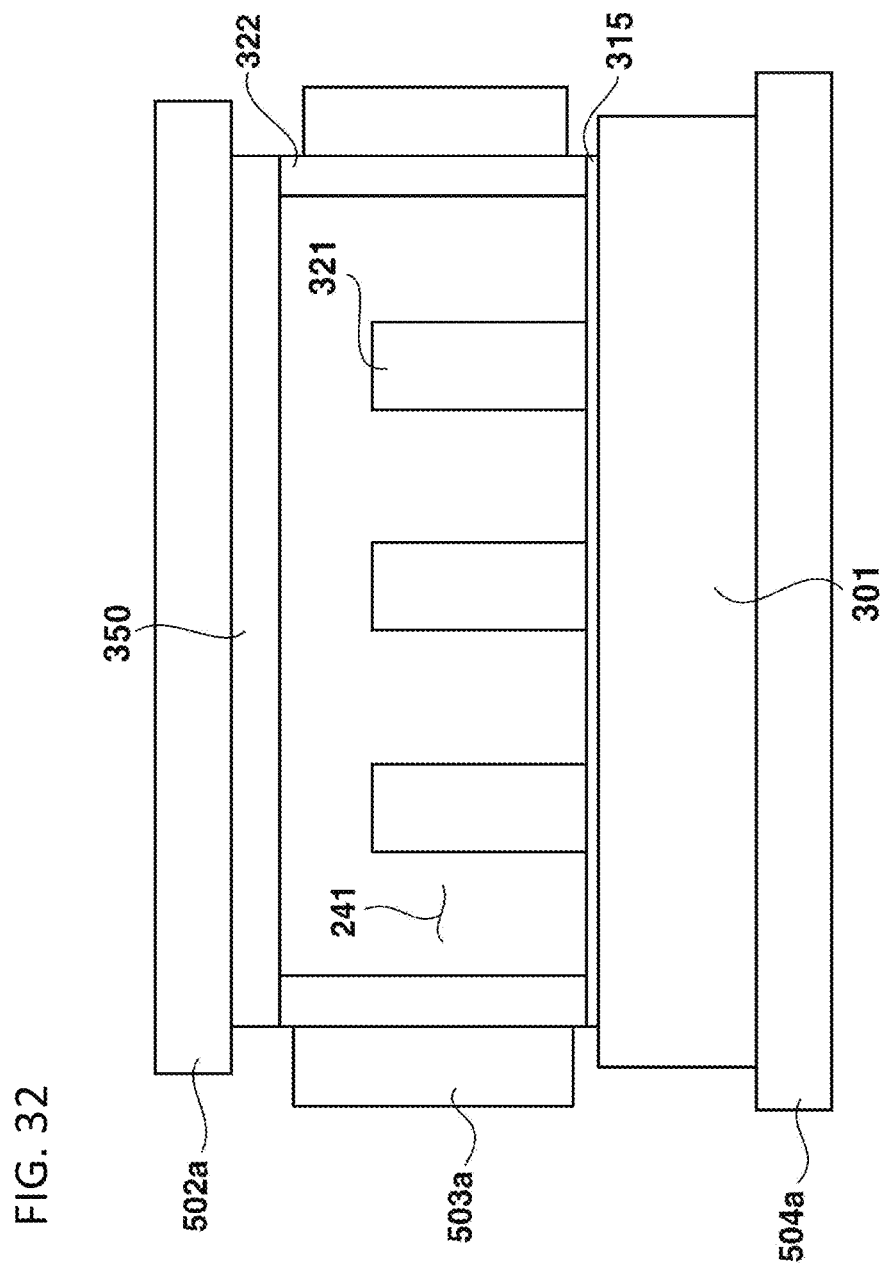
FIG. 32 is a cross-sectional view illustrating a PCR module according to further still another embodiment of the present invention.

FIG. 32 is a cross-sectional view illustrating a PCR module according to further still another embodiment of the present invention. The PCR module of FIG. 32 is substantially the same as shown in FIG. 25 except a first heat conductor 502*a*, a second heat conductor 504*a*, and an internal heat conductor 503*a*, and thus, any repetitive explanation concerning the above elements will be omitted.

Referring to FIG. 32, the PCR module further includes the first heat conductor 502*a*, the second heat conductor 504*a*, and the internal heat conductor 503*a*. The first heat conductor 502*a*, the second heat conductor 504*a*, and the internal heat conductor 503*a* may supply heat to the PCR module or dissipate heat toward an outside, thereby controlling temperature of the PCR module.

In the embodiment of the present invention, the first heat conductor 502*a* is disposed on a cover 350 to control an upper temperature of the PCR module. The second heat conductor 504*a* is disposed under a photo sensor assembly 301 to control a lower temperature of the PCR module. The internal heat conductor 503*a* is disposed on an outer surface of a partition wall 322 to control a temperature of a central portion of the PCR module.

In another embodiment of the present invention, the PCR module may only include one or two among the first heat conductor 502*a*, the second heat conductor 504*a*, and the internal heat conductor 503*a*.

Figure 33:
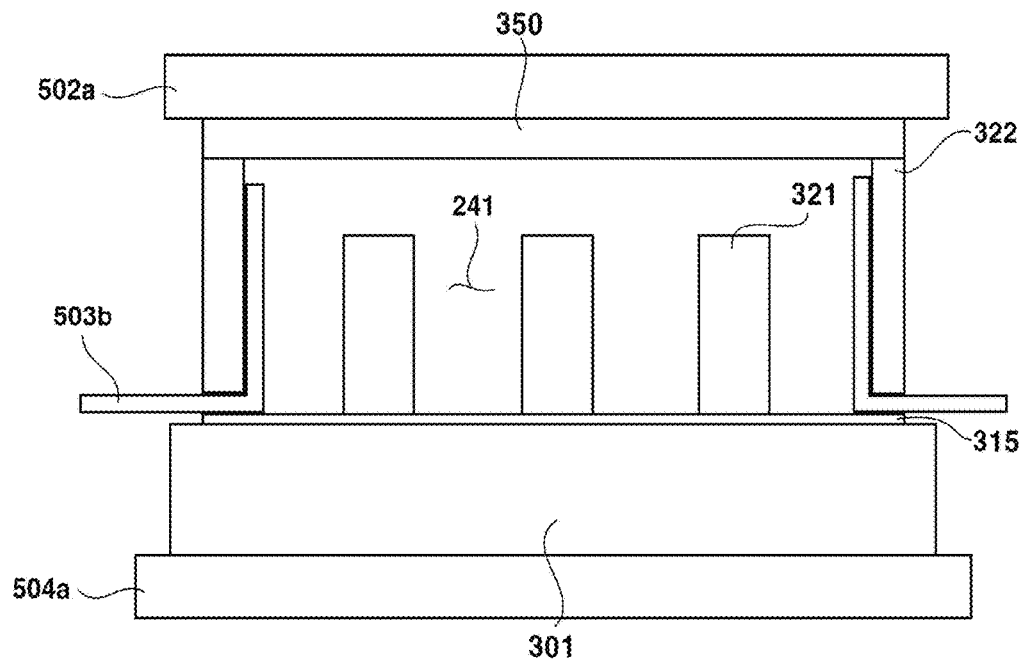
FIG. 33 is a cross-sectional view illustrating a PCR module according to further still another embodiment of the present invention.

FIG. 33 is a cross-sectional view illustrating a PCR module according to further still another embodiment of the present invention. The PCR module of FIG. 33 is substantially the same as shown in FIG. 32 except an internal heat conductor 503*b*, and thus, any repetitive explanation concerning the above elements will be omitted.

Referring to FIG. 33, a portion of the internal heat conductor 503*b* is disposed in the reaction space 241, and a remaining portion of the internal heat conductor 503*b* is protruded toward an outside of the reaction space 241. For example, a portion of the internal heat conductor 503*b* is disposed on an inner surface of a partition wall 322, and a remaining portion of the internal heat conductor 503*b* passes through the partition wall 322 and is protruded toward an outside of the reaction space 241.

The internal heat conductor 503*b* may include metal, diamond, metal oxide, etc. For example, the internal heat conductor 503*b* may include metal coating, transparent metal oxide such as indium tin oxide (ITO), etc.

In another embodiment of the present invention, the internal heat conductor 503*b* may be disposed on the partition wall 321 disposed in the reaction space 241.

Figure 34:
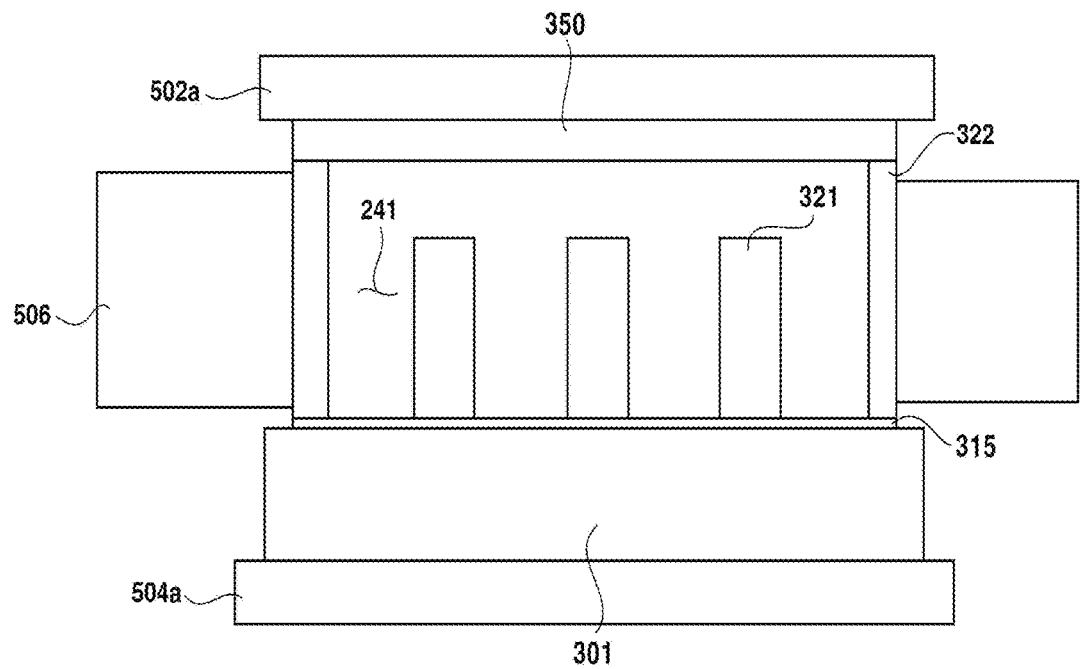
FIG. 34 is a cross-sectional view illustrating a PCR module according to further still another embodiment of the present invention.

FIG. 34 is a cross-sectional view illustrating a PCR module according to further still another embodiment of the present invention. The PCR module of FIG. 34 is substantially the same as shown in FIG. 32 except a heat conducting fluid 506, and thus, any repetitive explanation concerning the above elements will be omitted.

Referring to FIG. 34, the heat conducting fluid 506 is disposed on an outer surface of the partition wall 322. The heat conducting fluid 506 cools or heats the outside of the partition wall 322 to control temperature of a reaction space 241. For example, the heat conducting fluid 506 may be circulated by a pump (not shown).

Figure 35:
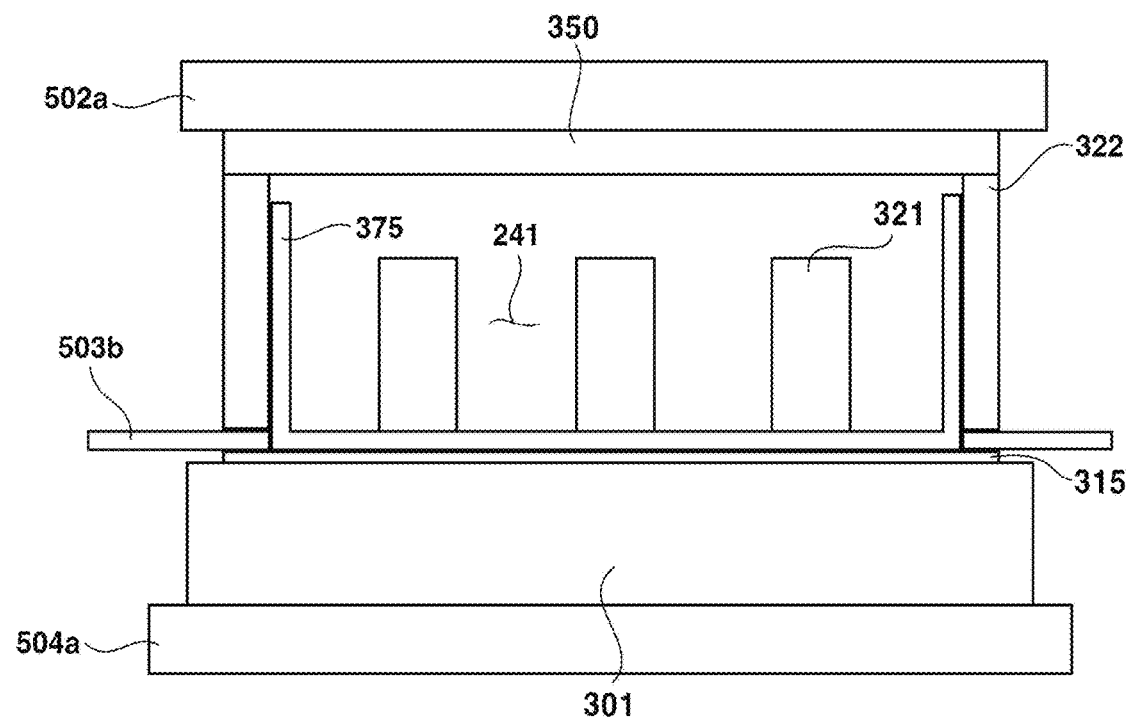
FIG. 35 is a cross-sectional view illustrating a PCR module according to further still another embodiment of the present invention.

FIG. 35 is a cross-sectional view illustrating a PCR module according to further still another embodiment of the present invention. The PCR module of FIG. 35 is substantially the same as shown in FIG. 32 except an internal heat conductor 503*b* and a heating part 375, and thus, any repetitive explanation concerning the above elements will be omitted.

Referring to FIG. 35, the internal heat conductor 503*b* is disposed at a central portion of the PCR module, and is protruded toward an outside of a reaction space 241. A first heat conductor 502*a*, a second heat conductor 504*a*, and the internal heat conductor 503*b* dissipate heat of the PCR module to the outside, thereby decreasing temperature of the reaction space 241.

The heating part 375 is disposed in the reaction space 241 to increase the temperature of the reaction space 241. In another embodiment of the present invention, the heating part 375 may be disposed on an upper surface of a cover 350, a lower surface of a photo sensor assembly 301, etc.

According to the embodiment of the present invention, the PCR module includes the heat conductors 502*a*, 503*b*, and 504*a* and the heating part 375 to easily control the temperature of the reaction space 241.

Figure 36:
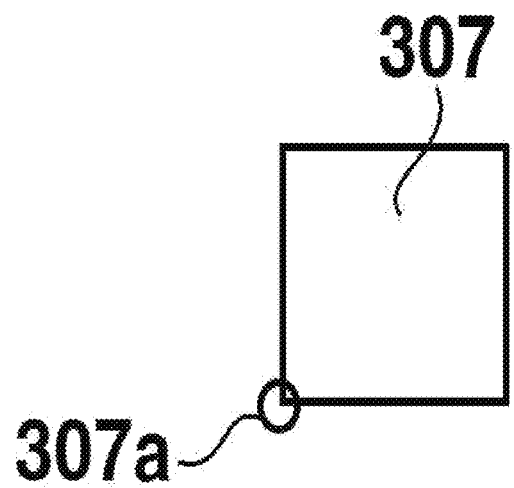
FIG. 36 is a plan view illustrating a photo sensor according to one embodiment of the present invention.

FIG. 36 is a plan view illustrating a photo sensor according to one embodiment of the present invention. The PCR module of FIG. 36 is substantially the same as shown in FIG. 25 except a photo sensor, and thus, any repetitive explanation concerning the above elements will be omitted.

Referring to FIG. 36, the photo sensor includes one photo sensor unit 307 and one output electrode 307*a*. In the embodiment of the present invention, the output electrode 307*a* corresponds to the photo sensor unit 307, so that a photo sensing signal generated from the photo sensor unit 307 is output through the output electrode 307*a*.

Figure 37:
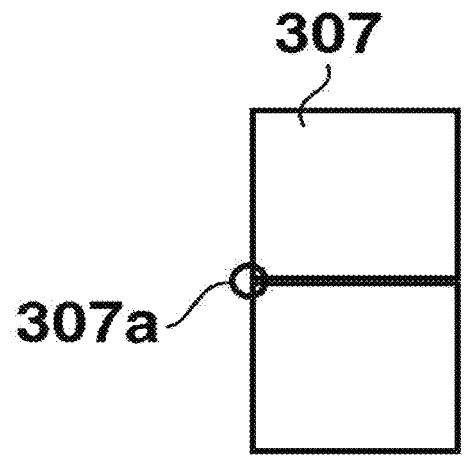
FIG. 37 is a plan view illustrating a photo sensor according to another embodiment of the present invention.

FIG. 37 is a plan view illustrating a photo sensor according to another embodiment of the present invention. The PCR module of FIG. 37 is substantially the same as shown in FIG. 36 except a photo sensor, and thus, any repetitive explanation concerning the above elements will be omitted.

Referring to FIG. 37, the photo sensor includes two photo sensor units 307 and one output electrode 307*a*. In the embodiment of the present invention, the output electrode 307*a* corresponds to the two photo sensor units 307, so that photo sensing signals generated from the two photo sensor units 307 are summed and output through the output electrode 307*a*.

Thus, a sensing sensitivity against the same amount of light irradiated onto the photo sensor shown in FIG. 36 is increased by twice.

Figure 38:
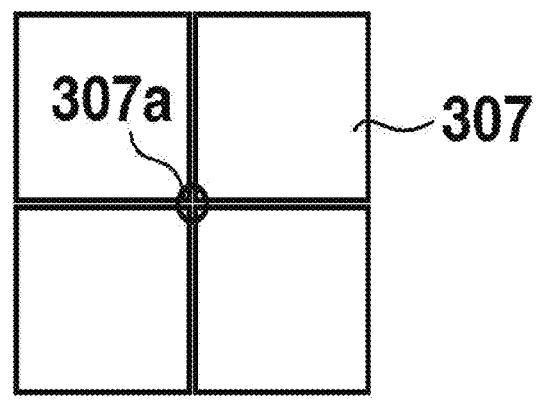
FIG. 38 is a plan view illustrating a photo sensor according to still another embodiment of the present invention.

FIG. 38 is a plan view illustrating a photo sensor according to still another embodiment of the present invention. The PCR module of FIG. 38 is substantially the same as shown in FIG. 36 except a photo sensor, and thus, any repetitive explanation concerning the above elements will be omitted.

Referring to FIG. 38, the photo sensor includes four photo sensor units 307 and one output electrode 307*a*. In the embodiment of the present invention, the output electrode 307*a* corresponds to the four photo sensor units 307, so that photo sensing signals generated from the four photo sensor units 307 are summed and output through the output electrode 307*a*.

Thus, a sensing sensitivity against the same amount of light irradiated onto the photo sensor shown in FIG. 36 is increased by four times.

Figure 39:
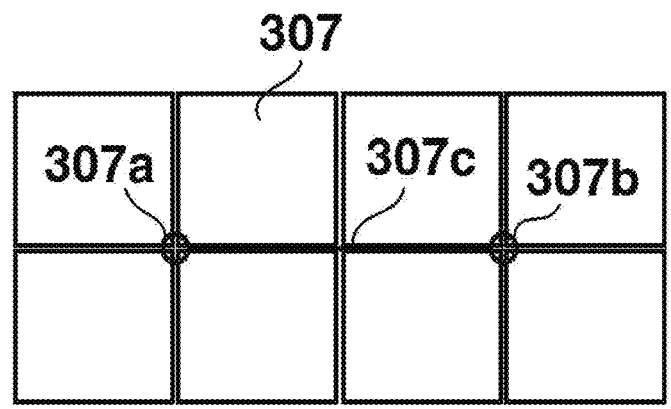
FIG. 39 is a plan view illustrating a photo sensor according to further still another embodiment of the present invention.

FIG. 39 is a plan view illustrating a photo sensor according to further still another embodiment of the present invention. The PCR module of FIG. 39 is substantially the same as shown in FIG. 36 except a photo sensor, and thus, any repetitive explanation concerning the above elements will be omitted.

Referring to FIG. 39, the photo sensor includes eight photo sensor units 307, two output electrodes 307a and 307b, and one connecting line 307c. In the embodiment of the present invention, overall output signal corresponds to the eight photo sensor units 307 through the one connecting line 307c and the two output electrodes 307a and 307b, so that photo sensing signals generated from the eight photo sensor units 307 is summed and output through as the one output signal.

Thus, a sensing sensitivity against the same amount of light irradiated onto the photo sensor shown in FIG. 36 is increased by eight times.

Figure 40:
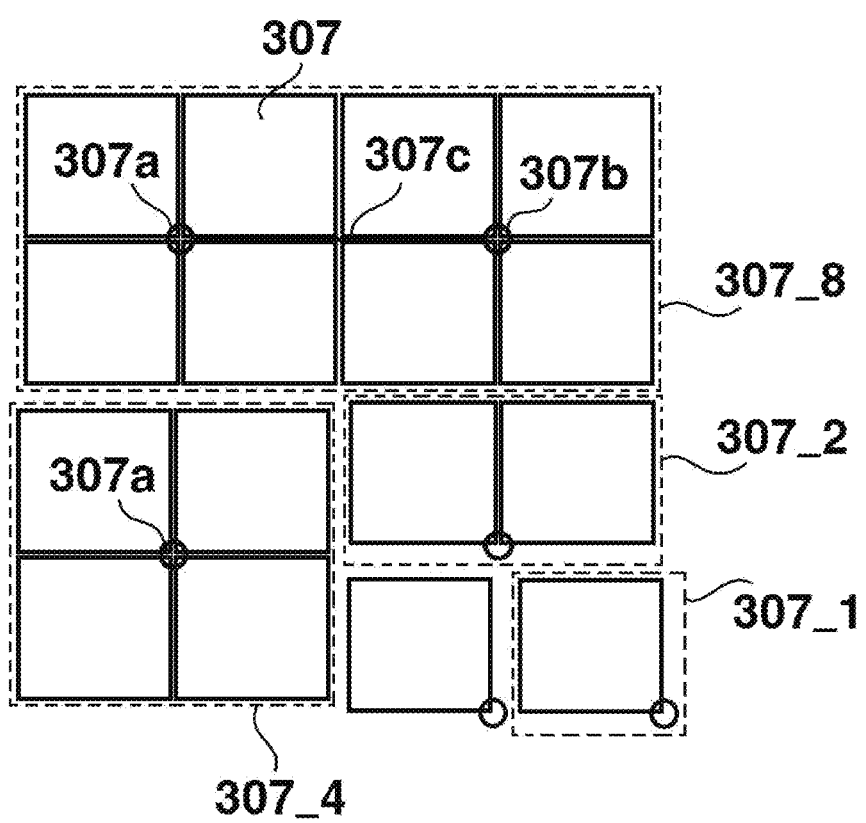
FIG. 40 is a plan view illustrating a photo sensor array manufactured by combining FIGS. 36 to 39.
Figure 41:
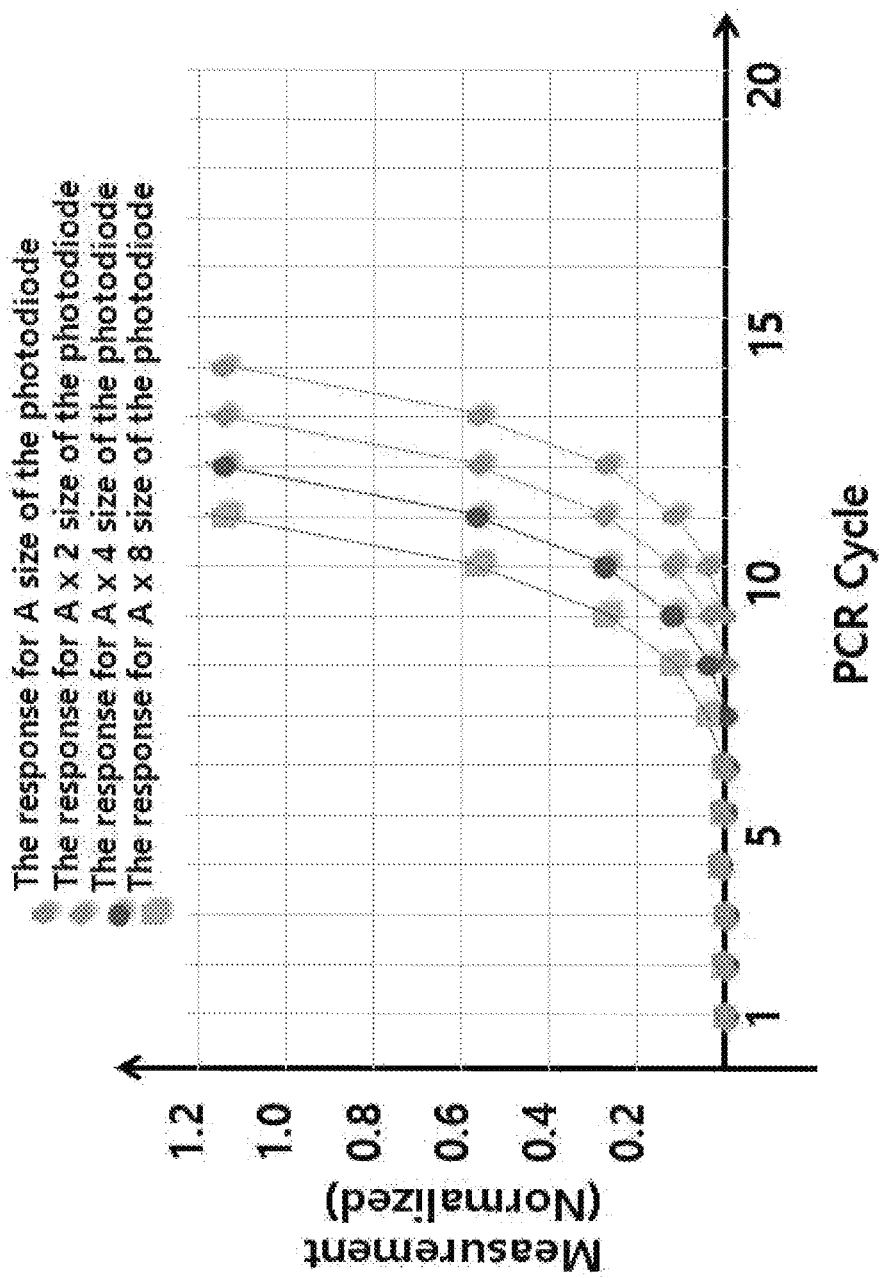
FIG. 41 is a graph illustrating output signals of the photo sensor array shown in FIG. 40.

FIG. 40 is a plan view illustrating a photo sensor array manufactured by combining FIGS. 36 to 39. FIG. 41 is a graph illustrating output signals of the photo sensor array shown in FIG. 40.

Referring to FIGS. 40 and 41, the photo sensor array includes two first photo sensors 307_1, a second photo sensor 307_2, a third photo sensor 307_4, and a fourth photo sensor 307_8.

In the embodiment of the present invention, the first photo sensors 307_1, the second photo sensor 307_2, the third photo sensor 307_3, and the fourth photo sensor 307_4 are substantially the same as shown in FIGS. 36 to 39, respectively.

Although the same light is irradiated, signals output from the first to fourth photo sensors 307_1, 307_2, 307_4, and 307_8 are different output signals having different amounts. As the number of photo sensor units included in one photo sensor 307_1, 307_2, 307_4, or 307_8 is increased, sensitivity of the photo sensor 307_1, 307_2, 307_4, or 307_8 is increased.

However, when the sensitivity of the photo sensor is increased too much, sensing capacity of the photo sensor may be easily saturated.

As described in the embodiment of the present invention, the photo sensor array includes the plurality of photo sensors 307_1, 307_2, 307_4, and 307_8 having the photo sensor units of different numbers, so that sensing capacity is optimized based on the intensity of the incident light. Also, accuracy of the photo sensor array is improved by the output signals output from the plurality of photo sensors 307_1, 307_2, 307_4, and 307_8.

Figure 42:
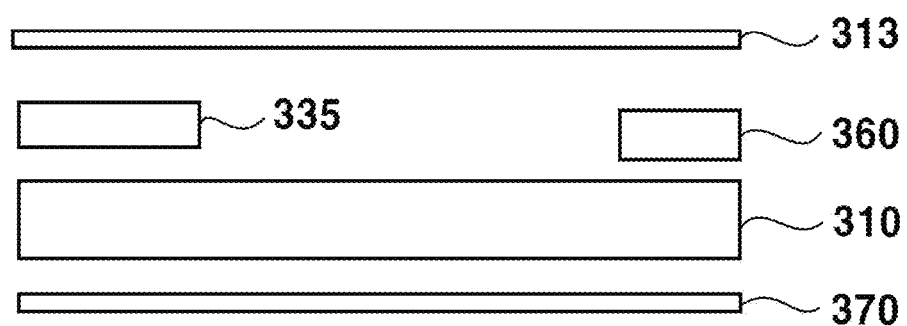
FIG. 42 is a cross-sectional view illustrating a photo sensor assembly according to one embodiment of the present invention.

FIG. 42 is a cross-sectional view illustrating a photo sensor assembly according to one embodiment of the present invention. The photo sensor assembly of FIG. 42 is substantially the same as shown in FIGS. 10 to 40 except a light source driving circuit, and thus, any repetitive explanation concerning the above elements will be omitted.

Referring to FIGS. 10 and 42, the photo sensor assembly includes a photo sensor array 310, a fluorescent filter 313, a first temperature control part 370, a temperature sensor 360, and a light source driving circuit 335.

The light source driving circuit 335 applies a driving power to a light source 331 (shown in FIG. 35) based on control of a reader system 100 or an interface member 390 (shown in FIG. 25).

Figure 43:
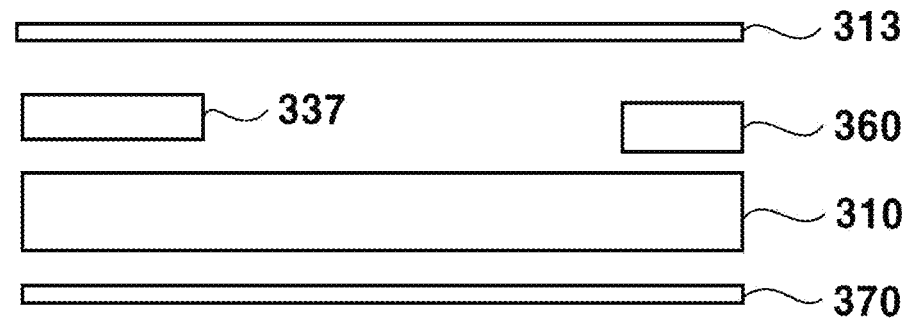
FIG. 43 is a cross-sectional view illustrating a photo sensor assembly according to another embodiment of the present invention.

FIG. 43 is a cross-sectional view illustrating a photo sensor assembly according to another embodiment of the present invention. The photo sensor assembly of FIG. 43 is substantially the same as shown in FIG. 42 except a driving circuit part, and thus, any repetitive explanation concerning the above elements will be omitted.

Referring to FIGS. 10 and 43, the photo sensor assembly includes a photo sensor array 310, a fluorescent filter 313, a first temperature control part 370, a temperature sensor 360, and a driving circuit part 337.

The driving circuit part 337 applies a driving power to a light source 331 (shown in FIG. 35) or controls signal input/out of the photo sensor assembly based on control of a reader system 100 or an interface member 390 (shown in FIG. 25).

According to the present invention, the optical part is embedded into the PCR module, and the PCR module is manufactured in a detachable module shape. Thus, size of the reader system is greatly decreased. Also, size of the PCR module and the reader system is greatly decreased, and manufacturing cost is decreased.

Also, although the reader system is moved, rearrangement, calibration, etc., is not required. Thus, mobility is greatly improved, so that point-of-care inspection is capable. In particular, in an emergency case such as epidemic, identification in disaster, etc., the PCR system may be rapidly introduced, so that damage may be decreased.

Also, the reagent may be embedded into the PCR module, so that additional process for setting the reagent may be omitted. Thus, pollution is greatly decreased, and an additional process for preparing inspection may be omitted.

Also, information communication to the outside may be possible through an internet, etc., so that a system such as an application store or a market may be established by various customers and a plurality of reagent developers. Thus, reagents and information may be exchanged.

Also, the PCR module includes the plurality of hydrogel pads, and different primers are disposed in the hydrogels. Thus, a plurality of gene types may be inspected.

Also, in a conventional multi inspection method, since different wavelengths of fluorescent lights are used, an optical part has complex structure. However, in the embodiment of the present invention, different primers are disposed in the hydrogel pads, so that the multi-inspection may be performed although single fluorescent material is used. Thus, the photo sensor assembly has a simple structure.

Also, the specimens and the buffering agent are alternately disposed in the specimen injection part, so that the specimens may be injected into the plurality of hydrogel pads by the simple operation of pressing the pressure from the one side of the specimen injection part.

Also, in a conventional array method, since genetic material is only disposed on a surface of a pad, the gene amplification speed is very slow. However, the hydrogel pad has the 3D structure of the polymer chains, so that the gene amplification is performed in the hydrogel pad as well as on the surface of the hydrogel pad. Thus, the gene amplification speed is very fast. Thus, the array may be formed by the hydrogel pads, so that the gene amplification may be performed in real time at various positions. Also, the fluorescent light is only generated from the hydrogel pad, so that the amount of light is increased to increase intensity of the signal, thereby realizing more sensitive test.

Also, the PCR module includes the heat conductor and the heating part, so that the temperature of the reaction space may be easily adjusted.

Furthermore, the PCR module may include the plurality of photo sensors having the photo sensor units of different numbers, so that optimized inspection based on the intensity of the light. Thus, accuracy is improved using the signals output from the plurality of photo sensors.

Also, the photo sensor assembly may include the light driving part or the driving circuit part, so that the size of the PCR system may be greatly decreased.

The present invention has an industrial applicability such as research of amplifying and inspecting genetic material, preventing disaster, medical purpose, livestock, veterinary medical care, etc.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present inventive concept. Accordingly, all such modifications are intended to be included within the scope of the present inventive concept as defined in the claims. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. A polymerase chain reaction (PCR) module detachably combined with a reader system including a central processing unit (CPU), a memory, and an interface, the CPU receiving a photo sensing signal to calculate gene amplification amount in real time and generating a temperature control signal based on a temperature signal and a temperature control information, the memory being connected to the CPU to store the gene amplification amount and the temperature control information, the interface being connected to the CPU to transmit the gene amplification amount received from the CPU in real time to an outside or to apply an external input signal to the CPU, the PCR module comprising:
 a photo sensor assembly including:
  a plurality of photo sensors arranged in an array shape to sense emission light generated from a specimen to generate the photo sensing signal; and
  a temperature sensor sensing temperature to output the temperature signal;
 a partition wall protruded from the photo sensor assembly to define a plurality of reaction spaces in which the specimen is received; and
 an interface module electrically connected to the photo sensor assembly to transmit the photo sensing signal and the temperature signal to the reader system,
 wherein a plurality of photo sensors corresponds to each of the reaction spaces,
 and wherein the photo sensor assembly includes a first photo sensor and a second photo sensor having different sensitivity from the first photo sensor, and the first and second photo sensors output different output signals having difference amounts, although the same light is irradiated on the first and second photo sensors.

2. The PCR module of claim 1, further comprising:
a light source supplying light to the reaction space;
an optical filter disposed on the photo sensor assembly to transmit the emission light; and
a cover defining an upper portion of the reaction space and including opaque material.

3. The PCR module of claim 1, wherein the reader system further comprises a light source supplying light to the reaction space, and the PCR module further comprises a cover defining an upper portion of the reaction space and including transparent material.

4. The PCR module of claim 1, wherein the reader system further comprises a temperature control module receiving the temperature control signal to adjust temperature of the reaction space.

5. The PCR module of claim 1, further comprising a temperature control part receiving the temperature control signal to adjust temperature of the reaction space, and wherein the interface module receives the temperature control signal to apply the received temperature control signal to the temperature control part.

6. The PCR module of claim 5, wherein the reader system further comprises:
 a heat conductor surrounding the PCR module; and
 a thermostatic member maintaining a constant temperature and exchanging heat with the heat conductor.

7. The PCR module of claim 5, the PCR module further comprises a heat conductor receiving the temperature control signal to transmit heat in the reaction space to the outside.

8. The PCR module of claim 5, wherein the PCR module further comprises a heating part receiving the temperature control signal to increase temperature of the reaction space.

9. The PCR module of claim 1, wherein one output electrode of the photo sensor is connected to a plurality of photo sensor units.

10. The PCR module of claim 9, wherein the photo sensor assembly further comprises a photo sensor array including a plurality of photo sensors having photo sensor units of different numbers.

11. The PCR module of claim 1, wherein the reader system is detachably combined with a plurality of PCR modules.

12. The PCR module of claim 1, further comprising a plurality of 3-dimensional (3D) organic pads disposed on the photo sensor assembly, each of the 3D organic pads including:
 a hydrophilic material being not melted or dissolved but being cross-linked by high polymer chains or polymer chains to form a 3D structure when mixed with water; and
 a primer being a small DNA attached to an area adjacent to gene nucleotide sequence to be amplified, and being a starting DNA when polymerase amplifies DNA,
 wherein the 3D organic pads correspond to the reaction spaces, respectively.

13. The PCR module of claim 12, wherein the 3D organic pad comprises a hydrogel pad or a spin on glass (SOG) pad.

14. The PCR module of claim 1, wherein the photo sensor assembly is electrically connected to the interface module through wire bonding.

15. A polymerase chain reaction (PCR) system comprising:
 a reader system including:
  a central processing unit (CPU) receiving a photo sensing signal to calculate gene amplification amount in real time and generating a temperature control signal based on a temperature signal and a temperature control information;
  a memory being connected to the CPU to store the gene amplification amount and the temperature control information; and an interface being connected to the CPU to transmit the gene amplification amount received from the CPU in real time to an outside or to apply an external input signal to the CPU; and a PCR module detachably combined with the reader system and including:
- a photo sensor assembly including a plurality of photo sensors arranged in an array shape to sense emission light generated from a specimen to generate the photo sensing signal, and a temperature sensor sensing temperature to output the temperature signal;
- a partition wall protruded from the photo sensor assembly to define a plurality of reaction spaces in which the specimen is received; and
- an interface module electrically connected to the photo sensor assembly to transmit the photo sensing signal and the temperature signal to the reader system, wherein a plurality of photo sensors corresponds to each of the reaction spaces, and wherein the photo sensor assembly includes a first photo sensor and a second photo sensor having different sensitivity from the first photo sensor, and the first and second photo sensors output different output signals having difference amounts, although the same light is irradiated on the first and second photo sensors.

16. The PCR system of claim 15, wherein the reader system further comprises a second temperature control module decreasing temperature of the PCR module using the temperature control signal, and the PCR module further comprises a first temperature control part increasing temperature of the PCR module using the temperature control signal.

* * * * *